United States Patent
Feyen et al.

(10) Patent No.: US 10,556,801 B2
(45) Date of Patent: Feb. 11, 2020

(54) PROCESS FOR THE PREPARATION OF A DEALUMINATED ZEOLITIC MATERIAL HAVING THE BEA FRAMEWORK STRUCTURE

(71) Applicant: BASF SE, Ludwigshafen am Rhein (DE)

(72) Inventors: Mathias Feyen, Laudenbach (DE); Stefan Maurer, Shanghai Pudong (CN); Ulrich Mueller, Neustadt (DE); Xinhe Bao, Dalian (CN); Weiping Zhang, Dalian (CN); Dirk de Vos, Holsbeek (BE); Hermann Gies, Sprockhoevel (DE); Feng-Shou Xiao, Changchun (CN); Yokoi Toshiyuki, Tokyo (JP); Bilge Yilmaz, New York, NY (US); Ryoichi Otomo, Yokohama (JP)

(73) Assignee: BASF SE, Ludwigshafen am Rhein (DE)

( * ) Notice: Subject to any disclaimer, the term of this patent is extended or adjusted under 35 U.S.C. 154(b) by 103 days.

(21) Appl. No.: 15/549,905

(22) PCT Filed: Feb. 11, 2016

(86) PCT No.: PCT/IB2016/050715
§ 371 (c)(1),
(2) Date: Aug. 9, 2017

(87) PCT Pub. No.: WO2016/128917
PCT Pub. Date: Aug. 18, 2016

(65) Prior Publication Data
US 2018/0022611 A1 Jan. 25, 2018

(30) Foreign Application Priority Data
Feb. 12, 2015 (WO) ................ PCT/CN2015/072867

(51) Int. Cl.
*C01B 39/46* (2006.01)
*B01J 29/70* (2006.01)
(Continued)

(52) U.S. Cl.
CPC ......... *C01B 39/026* (2013.01); *B01J 29/7007* (2013.01); *C01B 39/46* (2013.01);
(Continued)

(58) Field of Classification Search
CPC ....... C01B 39/026; C01B 39/48; C01B 39/46; B01J 29/7007; B01J 37/08; B01J 37/16;
(Continued)

(56) References Cited

U.S. PATENT DOCUMENTS 3,308,069 A 3/1967 Wadlinger et al.
4,554,145 A 11/1985 Rubin
(Continued)

FOREIGN PATENT DOCUMENTS

CN 102372548 B * 3/2012
EP 2906554 A1 * 8/2015 ........... C07D 401/14
(Continued)

OTHER PUBLICATIONS

Goodson, Challlenges and Strategies for Patenting New Solid State Forms, FISH, Sep. 2014 (Year: 2014).*
(Continued)

*Primary Examiner* — David M Brunsman
(74) *Attorney, Agent, or Firm* — Womble Bond Dickinson (US) LLP

(57) ABSTRACT

The present invention relates to a method for the preparation of a treated zeolitic material having a BEA framework structure including the steps of:
(i) providing a zeolitic material having a BEA framework structure, wherein the BEA framework structure includes $YO_2$ and $X_2O_3$, wherein Y is a tetravalent
(Continued)

element, and X is a trivalent element, and wherein the zeolitic material having a BEA framework structure is obtainable and/or obtained from an organotemplate-free synthetic process;

(ii) calcining the zeolitic material provided in step (i) at a temperature of 650° C. or more; and (iii) treating the calcined zeolitic material obtained from step (ii) with an aqueous solution having a pH of 5 or less, as well as to zeolitic materials per se preferably obtainable according to the inventive method and to their use, and to a process for converting oxygenates to olefins employing the inventive zeolitic materials.

12 Claims, 41 Drawing Sheets

(51) Int. Cl.
    C01B 39/02        (2006.01)
    C07C 1/20         (2006.01)
(52) U.S. Cl.
    CPC ............ C07C 1/20 (2013.01); B01J 2229/36
        (2013.01); B01J 2229/37 (2013.01); B01J
        2229/40 (2013.01); C01P 2002/86 (2013.01);
                                  C07C 2529/70 (2013.01)
(58) Field of Classification Search
    CPC .... B01J 37/30; B01J 2229/36; B01J 2229/37;
                        B01J 2229/40; C07C 1/20; C07C
                                      2529/70; C01P 2002/86
    See application file for complete search history.

(56)                References Cited

U.S. PATENT DOCUMENTS

| | | | |
|---|---|---|---|
| 4,642,226 | A | 2/1987 | Calvert et al. |
| 4,645,864 | A | 2/1987 | Chang et al. |
| 5,139,759 | A | 8/1992 | Cannan et al. |
| 8,232,296 | B2 * | 7/2012 | Briggner ............ C07D 401/14 514/333 |
| 2015/0343431 | A1 | 12/2015 | Parvulescu et al. |
| 2015/0353446 | A1 | 12/2015 | Feyen et al. |
| 2015/0353808 | A1 | 12/2015 | Kimura et al. |
| 2015/0361325 | A1 | 12/2015 | Kimura et al. |
| 2016/0060434 | A1 | 3/2016 | Reinicker et al. |
| 2016/0109067 | A1 | 4/2016 | Kimura et al. |
| 2016/0115140 | A1 | 4/2016 | Teles et al. |
| 2016/0122296 | A1 | 5/2016 | Parvulescu et al. |
| 2016/0145171 | A1 | 5/2016 | Spannhoff et al. |
| 2016/0176834 | A1 | 6/2016 | Teles et al. |
| 2016/0176835 | A1 | 6/2016 | Riedel et al. |
| 2016/0185741 | A1 | 6/2016 | Teles et al. |
| 2016/0221920 | A1 | 8/2016 | Maurer et al. |
| 2016/0264543 | A1 | 9/2016 | Vautravers et al. |
| 2016/0279621 | A1 | 9/2016 | Parvulescu et al. |
| 2016/0325228 | A1 | 11/2016 | Feyen et al. |
| 2016/0332152 | A1 | 11/2016 | Parvulescu et al. |
| 2017/0144137 | A1 | 5/2017 | Smith et al. |
| 2017/0275076 | A1 | 9/2017 | Edgington et al. |

FOREIGN PATENT DOCUMENTS

| | | |
|---|---|---|
| WO | WO 2010/043843 | 4/2010 |
| WO | WO 2010/146156 | 12/2010 |
| WO | WO 2012/137132 | 10/2012 |
| WO | WO 2014/060260 | 4/2014 |
| WO | WO 2014/094916 | 6/2014 |
| WO | WO 2014/114537 | 7/2014 |
| WO | WO 2014/114538 | 7/2014 |
| WO | WO 2014/154509 | 10/2014 |
| WO | WO 2014/174416 | 10/2014 |
| WO | WO 2014/199348 | 12/2014 |
| WO | WO 2014/199349 | 12/2014 |
| WO | WO 2015/018807 | 2/2015 |
| WO | WO 2015/018815 | 2/2015 |
| WO | WO 2015/022616 | 2/2015 |
| WO | WO 2015/022617 | 2/2015 |
| WO | WO 2015/022623 | 2/2015 |
| WO | WO 2015/022632 | 2/2015 |
| WO | WO 2015/025250 | 2/2015 |
| WO | WO 2015/032851 | 3/2015 |
| WO | WO 2015/048394 | 4/2015 |
| WO | WO 2015/048485 | 4/2015 |
| WO | WO 2015/048489 | 4/2015 |
| WO | WO 2015/048491 | 4/2015 |
| WO | WO 2015/048492 | 4/2015 |
| WO | WO 2015/059171 | 4/2015 |
| WO | WO 2015/059175 | 4/2015 |
| WO | WO 2015/067655 | 5/2015 |
| WO | WO 2015/083113 | 6/2015 |
| WO | WO 2015/091832 | 6/2015 |
| WO | WO 2015/094908 | 6/2015 |
| WO | WO 2015/094920 | 6/2015 |
| WO | WO 2015/101930 | 7/2015 |
| WO | WO 2015/123530 | 8/2015 |
| WO | WO 2015/123531 | 8/2015 |
| WO | WO 2015/144695 | 10/2015 |
| WO | WO 2015/162082 | 10/2015 |
| WO | WO 2015/162083 | 10/2015 |
| WO | WO 2015/169939 | 11/2015 |
| WO | WO 2015/185625 | 12/2015 |
| WO | WO 2015/185633 | 12/2015 |
| WO | WO 2016/024201 | 2/2016 |
| WO | WO 2016/037043 | 3/2016 |
| WO | WO 2016/038030 | 3/2016 |
| WO | WO 2016/058541 | 4/2016 |
| WO | WO 2016/066629 | 5/2016 |
| WO | WO 2016/074918 | 5/2016 |
| WO | WO 2016/075100 | 5/2016 |
| WO | WO 2016/075129 | 5/2016 |
| WO | WO 2016/075136 | 5/2016 |
| WO | WO 2016/128917 | 8/2016 |

OTHER PUBLICATIONS

Jenkins, "Diffraction Theory", Introduction to X-ray Powder Diffractometry, Wiley and Sons, 1996, pp. 47-95 (Year: 1996).*

Baran, R., et al., "Influence of the Nitric Acid Treatment on Al Removal, Framework Composition and Acidity of BEA Zeolite Investigated by XRD, FTIR and NMR," *Microporous and Mesoporous Materials*, 2012, vol. 163, pp. 122-130.

Beers, A. E. W., et al., "Optimization of zeolite Beta by steaming and acid leaching for the acylation of anisole with octanoic acid: a structure-activity relation," *Journal of Catalysis*, 2003, vol. 218, pp. 239-248.

Corma, A., et al., "Isobutane/2-butene alkylation on zeolite beta: Influence of post-synthesis treatments," *Applied Catalysis A: General*, 1996, vol. 142, pp. 139-150.

Kubota, Y., et al., "Effective Fabrication of Catalysts from Large-Pore, Multidimensional Zeolites Synthesized without Using Organic Structure-Directing Agents," *Chemistry of Materials*, 2014, vol. 26, pp. 1250-1259.

Majano, G., et al., "Al-Rich Zeolite Beta by Seeding in the Absence of Organic Template," *Chemistry of Materials*, 2009, vol. 21(18), pp. 4184-4191.

Muller, M., et al., "Comparison of the dealumination of zeolites beta, mordenite, ZSM-5 and ferrierite by thermal treatment, leaching with oxalic acid and treatment with SiCl4 by 1H, 29Si and 27 Al MAS NMR," *Microporous and Mesoporous Materials*, 2000, vol. 34, pp. 135-147.

Ong, L. H., et al., "Dealumination of HZSM-5 via Steam-Treatment," *Microporous and Mesoporous Materials*, 2012, vol. 164, pp. 9-20.

Roberge, D. M., et al., "Dealumination of zeolite Beta by acid leaching: A new insight with two dimensional multi-quantum and cross polarication 27 Al MAS NMR," *Physical Chemistry Chemical Physics*, 2002, vol. 4, pp. 3128-3135.

(56) References Cited

OTHER PUBLICATIONS

Srivastava, R., et al., "Dealumination of Zeolite Beta Catalyst Under Controlled Conditions for Enhancing its Activity in Acylation and Esterification," *Catalysis Letters*, 2009, vol. 130, pp. 655-663.
Xiao, B., et al., "Organotemplate-Free and Fast Route for Synthesizing Beta Zeolite," *Chemistry of Materials*, 2008, vol. 20(14), pp. 4533-4535.
De Baerdemaeker, T., et al., "Catalytic applications of OSDA-free Beta zeolite," *Journal of Catalysis*, 2013, vol. 308, pp. 73-81.
Heinichen, H. K., et al., "Acylation of 2-Methoxynaphthalene in the Presence of Modified Zeolite HBEA," *Journal of Catalysis*, 1999, vol. 185, pp. 408-414.
Yilmaz, B., et al., "A new catalyst platform: zeolite Beta from template-free synthesis," *Catalysis Science & Technology*, Oct. 2013, vol. 3(10), pp. 2580-2586.

\* cited by examiner

US 10,556,801 B2

PROCESS FOR THE PREPARATION OF A DEALUMINATED ZEOLITIC MATERIAL HAVING THE BEA FRAMEWORK STRUCTURE

CROSS-REFERENCE TO RELATED APPLICATIONS

This application is a national stage filing under 35 U.S.C. 371 of PCT/IB2016/050715, filed Feb. 11, 2016, which International Application was published by the International Bureau in English on Aug. 18, 2016, and application claims priority from International Application No. PCT/CN2015/072867, filed on Feb. 12, 2015, which applications are hereby incorporated in their entirety by reference in this application.

The present invention relates to a method for the preparation of a dealuminated zeolitic material having a BEA framework structure. Furthermore, the present invention relates to a zeolitic material as obtained or as obtainable according to the inventive process, as well as to a zeolitic material per se having a BEA framework structure and displaying the specific characteristics as found in the dealuminated zeolitic materials obtained according to the inventive method. Finally, the present invention relates to a process for the conversion of oxygenates to olefins employing the inventive zeolitic materials having a BEA framework structure as well as to the use of said materials in general, and in particular as a catalyst for the conversion of organic compounds.

INTRODUCTION

The most prominent and best studied example for a zeolitic material with a BEA framework structure is zeolite Beta, which is a zeolite containing $SiO_2$ and $Al_2O_3$ in its framework and is considered to be one of the most important nanoporous catalysts with its three-dimensional 12-membered-ring (12MR) pore/channel system and has been widely used in petroleum refining and fine chemical industries. Zeolite Beta was first described in U.S. Pat. No. 3,308,069 and involved the use of the tetraethylammonium cation as the structure directing agent. Although numerous alterations and improvements had since then been made to the preparation procedure, including the use of other structure directing agents such as dibenzyl-1,4-diazabicyclo[2,2,2]octane in U.S. Pat. No. 4,554,145 or dibenzylmethylammonium in U.S. Pat. No. 4,642,226, the known processes for its preparation still relied on the use of organic template compounds. In U.S. Pat. No. 5,139,759, for example, it is reported that the absence of an organic template compound in the synthetic procedure of zeolite Beta leads to the crystallization of ZSM-5 instead.

Recently, however, it has surprisingly been discovered that zeolite Beta and related materials may be prepared in the absence of the organotemplates which until then had always been used as structure directing agent. Thus, in Xiao et al., Chem. Mater. 2008, 20, pp. 4533-4535 and Supporting Information, a process for the synthesis of zeolite Beta is shown, in which crystallization of an aluminosilicate gel is conducted using zeolite Beta seed crystals. In WO 2010/146156 A the organotemplate-free synthesis of zeolitic materials having the BEA framework structure, and in particular to the organotemplate-free synthesis of zeolite Beta is described. In Majano et al., Chem. Mater. 2009, 21, pp. 4184-4191, on the other hand, Al-rich zeolite Beta materials having Si/Al ratios as low as 3.9 are discussed which may be obtained from reactions employing seeding in the absence of organic templates. Besides the considerable advantage of not having to use costly organotemplates which required subsequent removal from the microporous framework by calcination, the new organotemplate-free synthetic methodologies further allowed for the preparation of Al-rich zeolite Beta with unprecedentedly low Si/Al ratios.

Although notable progress has been made in the recent past with respect to the synthesis of new zeolitic materials having the BEA framework structure, there still remains a considerable need for the provision of new zeolitic materials having improved characteristics. This applies in particular in view of the numerous catalytic applications in which they are currently used. In industrial applications, zeolites with a tailored Si/Al molar ratio are a prerequisite for obtaining a maximized performance, and in particular an improved activity and/or selectivity. Usually, highly optimized zeolite crystallizations do sometimes not lead to the desired Si/Al ratio. Thus, the above-mentioned recently reported template-free synthesis of zeolite BEA in the absence of organotemplates, leads to products with a Si/Al ratio below 10. However, for various catalytic applications a high concentration of alumina is unfavorable.

Therefore, efficient dealumination procedures are required to adjust the number of charged sites and the acidity. A crucial parameter for the dealumination of zeolites is the efficiency of the dealumination, describing the amount of alumina which can be removed in one cycle relative to the maintenance of the initial crystallization degree. If the parameters used in the dealumination process are not well adjusted, the zeolite may either be degraded during the process or the amount of removed Al-species within one cycle may be too low.

In this respect, commonly used dealumination procedures involve the treatment of the zeolite powder in acid media or a combination of a high temperature treatment step in the presence of $H_2O$, called steaming, with a subsequent treatment in acidic media. Thus Kubota, Y. et al. in Chem. Mater. 2014, 26, 1250-1259, relates to the dealumination of zeolite Beta obtained from organotemplate-free synthesis by heating with nitric acid, wherein the zeolitic material is stabilized by a steaming process performed prior to the dealumination step. Baran, R. et al. in Micropor. Mesopor. Mater., 2012, 163, 122-130, on the other hand, investigate the dealumination process in zeolite beta using nitric acid, wherein zeolite beta was obtained from synsthesis with an organotemplate. Ong, L. H. et al. in Micropor. Mesopor. Mater. 2012, 164, 9-20, relates to the dealumination of HZSM-5 using a steaming process. WO 2010/043843 describes the dealumination of a zeolite by impregnation with a univalent metal followed by a steaming step.

Corma et al., "*Isobutane/2-butene alkylation on zeolite beta: Influence of post-synthesis treatments*", Applied Catalysis A: General, vol. 142, 1996, pages 139-150, relate to the treatment of zeolite beta by successive calcination and ammonia exchange steps, as a result of which some framework dealumination is observed, followed by a dealumination treatment performed with hydrochloric aced, ammonium hexafluorosilicate, and steam, wherein zeolite beta was again obtained from synthesis with an organotemplate. Beers A E W et al., "*Optimization of zeolite Beta by steaming and acid leaching for the acylation of an/sole with octanoic ace: a structure-activity relation*", Journal of Catalysis, vol. 218, 2003, pages 239-248, describes the dealumination of a commercial zeolite beta by hydrochloric or oxalic acid and steaming. Muller M et al., "*Comparison of the dealumination of zeolites beta, mordenite, ZSM-5 and ferrierite by* thermal treatment, leaching with oxalic acid and treatment with SiCl$_4$ by $^1$H, $^{29}$Si and $^{27}$Al MAS NMR", Microporous and Mesoporous Materials, vol. 34, 2000, pages 135-147, describes the dealumination of a zeolite beta by acid leaching combined with steaming.

Rajendra Srivastava et al., "*Dealumination of zeolite Beta Catalyst under controlled conditions for enhancing its activity in acylation and esterification*", Catalysis Letters, vol. 130, 2009, pages 655-663, relates to the dealumination of zeolite beta using oxalic or tartaric acid solutions. Roberge D M et al., "*Dealumination of zeolite Beta by acid leaching: A new insight with two dimensional multi-quantum and cross polarization $^{27}$Al MAS NMR*", Physical Chemistry Chemical Physics, vol. 4, 2002, pages 3128-3135, concerns the investigation of the influence of acid leaching on commercial zeolite beta with concentrated solutions of HCl and HNO$_3$. Finally, WO 2012/137132 A1 relates to a process for the dealumination of a zeolitic material having a BEA type framework structure involving one or more steam- and/or acid-treatment steps.

Despite the numerous existing methods for the dealumination of zeolitic materials, the problem nevertheless remains that both acid treatment and steaming at high temperatures of zeolite beta for its dealumination results in an instability of the zeolite framework due its chemical dissolution and the thermal strain it is exposed to, respectively.

DETAILED DESCRIPTION

Therefore, it is the object of the present invention to provide a process for the removal of framework heteroatoms from a zeolitic material and in particular of aluminum therefrom wherein the instability resulting from the removed framework elements is minimized. Thus, it has quite surprisingly been found that by subjecting a zeolitic material obtained from an organotemplate-free synthetic process to a calcination procedure performed in the absence of steam, wherein said calcination procedure is followed by an acidic treatment of the calcined zeolitic material, a dealuminated zeolitic material may be obtained which displays a highly unexpected stability in particular with respect to exposure to high temperatures. In particular, it has quite unexpectedly been found that such a material displays a very low deactivation rate when employed in catalytic conversion reactions performed at high temperatures, thus, affording a catalytic material which displays sustained activity and selectivity in catalyzed conversion reactions during extended periods of time on stream. Said results are particularly surprising relative to zeolitic materials obtained from organotemplate-free synthesis and in particular zeolitic material having the BEA framework structure in view of the fact that said materials contain particularly high amounts of aluminum compared to conventional zeolitic materials as obtained from synthetic methods employing organotemplates, such that it would normally be expected that their dealumination leads to an increased instability of their zeolitic framework and thus to a particularly poor thermostability after dealumination thereof.

Thus, without wanting to be bound to the theory, it is tentatively assumed that as opposed to a steam treatment procedure as taught in the prior art for the dealumination of zeolitic materials, wherein the water content of the gas results in the extraction of the alumina species from the framework structure, calcination performed in the absence of water only leads to a partial removal of the alumina from their initial framework positions without however extracting them from the framework structure. Far more, according to the inventive process, said extraction is first achieved in the subsequent step of acidic treatment of the calcined framework structure, wherein said treatment for the dissolution of the aluminum species is performed at far lower temperatures than the foregoing calcination. As a result, it is tentatively assumed that as opposed to dealumination by steaming, the extraction of the aluminum species according to the present invention may be performed at comparatively low temperatures such that the dealuminated framework is not damaged by thermal strain as encountered in steaming regimens. Consequently, the resulting material may maintain a highly intact framework structure which is less prone to thermal degradation in future applications than dealuminated structures obtained from steaming which undergo partial degradation by being exposed to high thermal strain subsequent to the at least partial removal of aluminum from the framework structure.

Therefore, the present invention relates to a method for the preparation of a treated zeolitic material having a BEA framework structure comprising the steps of:
  (i) providing a zeolitic material having a BEA framework structure, wherein the BEA framework structure comprises YO$_2$ and X$_2$O$_3$, wherein Y is a tetravalent element, and X is a trivalent element, and wherein the zeolitic material having a BEA framework structure is obtainable and/or obtained from an organotemplate-free synthetic process;
  (ii) calcining the zeolitic material provided in step (i) at a temperature of 650° C. or more;
  (iii) treating the calcined zeolitic material obtained from step (ii) with an aqueous solution having a pH of 5 or less.

According to the inventive method, the zeolitic material having a BEA framework structure provided in (i) is obtainable and/or obtained from an organotemplate-free synthetic process. Accordingly, as regards the zeolitic material having a BEA framework structure which is obtained from an organotemplate-free synthetic process, at no point does the process employed for its synthesis involve the use of an organic structure directing agent and in particular an organic structure directing agent specifically used in the synthesis of zeolitic materials having a BEA-type framework structure, in particular specific tetraalkylammonium salts and/or related organotemplates such as tetraethylammonium and/or dibenzolmethylammonium salts, and dibenzol-1,4-diazabicyclo[2,2,2]octane. This applies in particular with respect to the reaction mixture employed for the crystallization of the zeolitic material having a BEA framework structure which at no point contains more than an impurity of an organic structure directing agent specifically used in the synthesis of zeolitic materials having a BEA-type framework structure and in particular one or more of the aforementioned specific organic structure directing agents. Such an impurity can, for example, be caused by organic structure directing agents still present in seed crystals used in the synthetic method for obtaining the zeolitic material having a BEA framework structure provided in step (i). Organotemplates contained in seed crystals may not, however, participate in the crystallization process since they are trapped within the seed crystal framework and therefore may not act as structure directing agents within the meaning of the present invention.

Therefore, in addition thereto or alternatively to providing a zeolitic material having a BEA framework structure obtained from an organotemplate-free synthetic process, a zeolitic material having a BEA framework structure may be provided in step (i) which is obtainable from an organotemplate-free synthetic process. Within the meaning of the present invention, the term "obtainable" refers to any zeolitic material having a BEA-type framework structure which is either obtained by an organotemplate-free synthetic process and in particular an organotemplate-free synthetic process as defined in the foregoing, or by any conceivable process which leads to a zeolitic material having a BEA-type framework structure as is obtainable to the inventive process, without however necessarily involving organotemplate-free synthesis. In particular, concerning zeolitic materials having a BEA framework structure obtainable from an organotemplate-free synthetic process provided in step (i), it is preferred that said zeolitic material has an X-ray diffraction pattern comprising at least the following reflections:

| Intensity (%) | Diffraction angle 2θ/° [Cu K(alpha 1)] |
|---|---|
| [11-31] | [21.07-21.27] |
| 100 | [22.12-22.32] |
| [13-33] | [25.01-25.21] |
| [17-37] | [25.53-25.73] |
| [13-33] | [26.78-26.98] |
| [11-31] | [28.39-28.59] |
| [22-42] | [29.24-29.44] |
| [6-26] | [30.00-30.20] |
| [9-29] | [32.86-33.26] |
| [11-31] | [42.90-43.30] | wherein 100% relates to the intensity of the maximum peak in the X-ray Potter diffraction pattern. Preferably, the zeolitic material having a BEA framework structure provided in step (i) has an X-ray diffraction pattern comprising at least the following reflections:

| Intensity (%) | Diffraction angle 2θ/° [Cu K(alpha 1)] |
|---|---|
| [11-31] | [21.12-21.22] |
| 100 | [22.17-22.27] |
| [13-33] | [25.06-25.16] |
| [17-37] | [25.58-25.68] |
| [13-33] | [26.83-26.93] |
| [11-31] | [28.44-28.54] |
| [22-42] | [29.29-29.39] |
| [6-26] | [30.05-30.15] |
| [9-29] | [33.01-33.11] |
| [11-31] | [43.05-43.15] | wherein 100% relates to the intensity of the maximum peak in the X-ray diffraction pattern.

In step (iii) of the inventive method, the one or more calcined zeolitic materials from step (2) are treated with an aqueous solution having a pH of 5 or less. As regards the pH of the aqueous solution employed therein, said pH value refers to the pH of the aqueous solution prior to contacting with the calcined zeolitic material and may be determined according to any suitable method for the determination of the pH of an aqueous solution. According to the present invention it is however preferred that the pH of the aqueous solution used in step (iii) is opbtained wherein it is particularly preferred that the pH is measured according to the international standard ISO 34-8 (International Standard ISO 34-8: Quantities and Units—Part 8: Physical Chemistry and Molecular Physics, Annex C (normative): pH. International Organization for Standardization, 1992). According to the present invention it is yet further preferred that the pH values as defined in the present application are determined in accordance with ISO 80000-9, Annex C, pH.

According to the inventive method, the one or more zeolitic materials provided in step (i) are calcined at a temperature of 650° C. or more and subsequently treated in step (iii) with an aqueous solution having a pH of 5 or less. According to the inventive method, no particular restrictions apply relative to the number and types of steps which it may include, nor relative to the presence or absence of additional steps between step (i) and step (ii), and between step (ii) and step (iii) as well as and in particular after step (iii) as further defined in particular and preferred embodiments thereof below. It is however preferred according to the inventive method that no additional steps are performed between steps (ii) and (iii). Thus, it is particularly preferred that the one or more calcined zeolitic materials are directly subject to the treatment with an aqueous solution having a pH of 5 or less in step (iii).

According to the inventive method, there is no particular restriction as to the number and/or types of zeolitic materials having a BEA framework structure which may be provided in step (i), provided that their respective BEA framework structure comprises $YO_2$ and $X_2O_3$, wherein Y is a tetravalent element and X is a trivalent element, wherein the zeolitic material is obtainable and/or obtained from an organotemplate-free synthetic process. It is, however, preferred according to the inventive method that the zeolitic material having a BEA framework structure comprises 5 wt.-% or less of one or more non-framework cationic elements other than H+ and/or $NH^{4+}$. more preferably, the zeolitic material having a BEA framework structure comprises 3 wt.-% or less of one or more non-framework cationic elements other than H+ and/or $NH^{4+}$, and more preferably 2 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, and more preferably 0.005 wt.-% or less. It is particularly preferred according to the inventive method that the zeolitic material having a BEA framework structure comprises 0.001 wt.-% or less of one or more non-framework cationic elements other than $H^+$ and/or $NH^{4+}$. As regards the amount of the one or more framework cationic elements in weight percent, said value is based on 100 wt.-% of the zeolitic material provided in step (i). Furthermore, as regards the term "non-framework" and in particular "non-framework element" and "non-framework cationic element", said term refers to any element or ion contained in the zeolitic material having a BEA framework structure which is not a constituting element of the framework structure, meaning that it is for example contained in the micropores of the structure and/or that it only serves to compensate the structural framework, for example as counterion or the like. Furthermore, said term also refers to originally constituting elements or ions of the BEA framework structure which have been altered from their original coordination state. In particular, a non-framework element X may refer to X originally contained in the framework structure as a constituting element, and in particular as tetrahedrally coordinated X in the BEA framework, and which has been subsequently removed from the framework structure, for example by a change in its original coordination state and/or by being contained in the micropores of the zeolitic material as opposed to the framework thereof.

Concerning the non-framework cationic elements other than H+ and/or $NH_4^+$ which may be contained in the zeolitic material having a BEA framework structure provided in step (i), no particular restriction applies neither with respect to the type nor with respect to the number of the non-framework cationic elements which may be contained therein. It is however preferred that the non-framework cationic element is Na or K, wherein more preferably the one or more non-framework cationic elements are Na and K. According to the inventive method it is yet further preferred that the one or more non-framework elements are selected from the group consisting of Li, Na, K, and combinations of two or three thereof, and more preferably from the group consisting of Li, Na, K, Rb, Cs, and combinations of two or more thereof, wherein yet more preferably the one or more non-framework elements are selected from the group consisting of alkali metals, alkaline earth metals, and combinations of two or more thereof. According to the inventive method it is particularly preferred that the one or more non-framework elements are selected from the group consisting of cationic elements other than $H+$ and/or $NH^{4+}$. As concerns the term "cationic element" as employed in the present application, said term preferably refers to any conceivable atomic element in its cationic form which may be selected from metals, metalloids, and non-metals. According to the present invention it is however preferred that the term "cationic element" refers to a metal and/or metalloid cation and preferably to a metal cation.

As regards the calcination of the zeolitic material in step (ii), no particular restrictions apply relative to the temperature of calcination provided that a temperature of 650° C. or more is employed at least during a certain portion of the calcination procedure. It is however preferred that the calcination of the zeolitic material provided in step (i) in step (ii) is conducted at a temperature comprised in the range of from 680° C. to 1000° C. It is further preferred that in step (ii) the zeolitic material provided in step (i) is calcined at a temperature comprised in the range of from 700° C. to 900° C., and more preferably of from 720° C. to 850° C., and more preferably of from 750° C. to 830° C. According to the inventive process it is particularly preferred that in step (ii) the zeolitic material provided in step (i) is calcined at a temperature comprised in the range of from 790° C. to 810° C.

Concerning the duration of the calcining in step (ii), no particular restriction applies such that any suitable duration of calcination may be chosen. Thus, by way of example, calcining in step (ii) may be conducted for a duration of anywhere from 0.5 to 72 h, wherein preferably calcining in step (ii) is conducted for a duration of from 1 to 64 h, and more preferably from 2 to 56 h. More preferably, calcining in step (ii) is conducted for a duration of from 4 to 48 h, more preferably of from 8 to 40 h, more preferably of from 12 to 36 h, and more preferably of from 16 to 32 h. According to the inventive method it is particularly preferred that the calcining in step (ii) is conducted for a duration of from 20 to 28 h. As regards the duration of the calcining according to any of the aforementioned particular and preferred embodiments, it is noted that the duration of the calcining refers to the total duration during which the zeolitic material provided in step (i) is calcined at a temperature of 650° C. or more.

As noted above, as opposed to the dealumination procedures known in the art, the inventive method does not involve a step of steaming, i.e. a thermal treatment of the zeolitic material having a BEA framework structure at an elevated temperature such as those encountered in a calcination procedure yet performed in the presence of steam which is brought into contact with the zeolitic material at those temperatures. As opposed to this, the inventive method involves a step of calcination in step (ii) at a temperature of 650° C. or more. Thus, the inventive method and in particular the step of calcining in step (ii) is performed in the absence of steam and in particular in the absence of notable amounts of water in the atmosphere employed in the calcination step. Thus, according to the inventive method, calcining in step (ii) is conducted in the absence of steam. Thus, the atmosphere under which calcining in step (ii) is conducted displays low levels of atmospheric moisture at a temperature of 650° C. at which calcining is performed, wherein preferably calcining in step (ii) is conducted in an atmosphere containing 10 wt.-% or less of water. More preferably, calcining in step (ii) is conducted in an atmosphere containing 5 wt.-% or less of water, more preferably 3 wt.-% or less, more preferably 2 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, and more preferably 0.005 wt.-% or less. According to the present invention it is particularly preferred that calcining in step (ii) is conducted in an atmosphere containing 0.001 wt.-% or less of water.

In step (iii) of the inventive method, the calcined zeolitic material obtained from step (ii) is treated with an aqueous solution having a pH of 5 or less. In particular, there is no particular restriction according to the present invention as to the pH of the aqueous solution with which the calcined zeolitic material is treated, provided that it does not exceed a pH of 5. Thus, by way of example, the pH of the aqueous solution employed in step (iii) may be comprised anywhere in the range of from −2 to 4, wherein preferably the pH of the aqueous solution is comprised in the range of from −1.8 to 3, more preferably of from −1.6 to 2, more preferably of from −1.4 to 1, more preferably of from −1.2 to 0.5, and more preferably of from −1 to 0.2. According to the present invention it is particularly, preferred that the pH of the aqueous solution employed in step (iii) is comprised in the range of from −0.8 to 0.

As regards the aqueous solution employed in step (iii) of the inventive method, no particular restriction applies as to the amount of water which it may contain, such that in principle any suitable aqueous solution may be employed provided that it contains water. Thus, by way of example, the aqueous solution employed in step (iii) may contain 50 wt.-% or more of water based on the total weight of the one or more solvents in the solution, wherein preferably the aqueous solution employed in step (iii) contains 60 wt.-% or more of water, and more preferably 70 wt.-% or more of water, more preferably 80 wt.-% or more, more preferably 90 wt.-% or more, more preferably 95 wt.-% or more, more preferably 98 wt.-% or more, and more preferably 99 wt.-% or more. According to the present invention it is particularly preferred that the aqueous solution employed in step (iii) contains 99.9 wt.-% or more of water based on the total weight of the one or more solvents in the solution, wherein even more preferably water is used as the solvent in the aqueous solution employed in step (iii). Within the meaning of the present invention, the term "water" preferably designates distilled water.

Concerning the aqueous solution employed in step (iii) of the inventive method, no particular restriction applies relative to the one or more acidic compounds which it may contain for achieving a pH of 5 or less. Thus, by way of example, the aqueous solution employed in step (iii) may contain any one or more acids selected from the group consisting of Bronsted acids and Lewis acids, wherein preferably the one or more acids are selected from the group consisting of Bronsted acids, and more preferably from the group consisting of inorganic Bronsted acids. As regards the specific Bronstedt acids and in particular the specific inorganic Bronstedt acids which may be preferably employed as the one or more acids in the aqueous solution employed in step (iii), no particular restrictions apply, such that said one or more acids may for example be selected from the groups consisting of phosphoric acid, sulphuric acid, hydrochloric acid, nitric acid, and mixtures of any two or more thereof. According to the inventive method it is however particularly preferred that the one or more acids contained in the aqueous solution employed in step (iii) are selected from the group consisting of sulphuric acid, hydrochloric acid, nitric acid, and mixtures of two or more thereof, wherein more preferably the aqueous solution employed in step (iii) contains hydrochloric acid and/or nitric acid. According to the inventive method, it is particularly, preferred that an aqueous solution of nitric acid is employed in step (iii).

As regards the treatment of the calcined zeolitic material in step (iii) with an aqueous solution having a pH of 5 or less, no particular restriction applies relative to the temperature at which said treatment may be preformed such that, by way of example, said treatment may be conducted at a temperature comprised in the range of anywhere from 25° C. up to the boiling point of the aqueous solution under standard atmospheric pressure, i.e. under an atmospheric pressure of 100.0 kPa. It is, however, preferred according to the inventive method that the treatment of the calcined zeolitic material with an aqueous solution having a pH of 5 or less in step (iii) is conducted at a temperature comprised in the range of from 30 to 100° C., more preferably of from 40 to 95° C., and more preferably of from 50 to 90° C. According to the present invention it is particularly preferred that the treatment of the calcined zeolitic material with an aqueous solution having a pH of 5 or less in step (iii) of the inventive method is conducted at a temperature comprised in the range of from 70 to 80° C.

Further concerning the treatment of the calcined zeolitic material obtained from step (ii) in an aqueous solution having a pH of 5 or less, no particular restrictions apply relative to the amount of the aqueous solution employed relative to the zeolitic material which is treated therewith. Thus, by way of example, the weight ratio of the aqueous solution having a pH of 5 or less to the zeolitic material in step (iii) may be comprised in the range of anywhere from 1 to 500. Preferably, however, the weight ratio of the aqueous solution having a pH of 5 or less to the zeolitic material in step (iii) is comprised in the range of from 5 to 300, more preferably from 10 to 200, more preferably from 20 to 150, more preferably from 30 to 100, more preferably from 35 to 80, and more preferably from 40 to 60. According to the present invention it is particularly preferred that in step (iii) the weight ratio of the aqueous solution having a pH of 5 or less to the zeolitic material is comprised in the range of from 45 to 55.

Finally, as regards the duration of the treatment in step (iii) of the inventive method, again, no particular restrictions apply such that the treatment of the calcined zeolitic material with an aqueous solution having a pH of 5 or less may be conducted for a period of anywhere from 0.25 to 48 h. Preferably, the treatment of the calcined zeolitic material with an aqueous solution having a pH of 5 or less is conducted for a period of from 0.5 to 24 h, more preferably of from 1 to 12 h, more preferably of from 1 to 6 h. According to the present invention it is particularly preferred that the treatment of the calcined zeolitic material with an aqueous solution having a pH of 5 or less in step (iii) is conducted for a period of from 1.5 to 3.5 h.

As noted in the foregoing, the inventive method is not particularly restricted with respect to the number of steps which it may contain and in particular with respect to additional steps in addition to steps (i), (ii), and (iii). In particular, the inventive method may comprise additional steps performed after step (iii) for the workup of the calcined zeolitic material after treatment thereof with an aqueous solution having a pH of 5 or less. In principle, any suitable workup steps may be employed for obtaining the final treated zeolitic material having a BEA framework structure. Thus, it is preferred that the inventive method according to any of the particular and preferred embodiments thereof further comprises the steps of:

(iv) isolating the zeolitic material obtained in step (iii),
(v) optionally washing the zeolitic material obtained in step (iii) or (iv); and/or,
(vi) optionally drying the zeolitic material having a BEA framework structure as obtained in steps (iii) or (iv) or (v).

As regards the preferred step (iv) of isolating the zeolitic material obtained in step (iii), this may be achieved by any suitable procedure wherein according to the present invention the isolating of the zeolitic material obtained in step (iii) is preferably achieved by filtration thereof. With respect to the particular means of filtration which may be employed, again no particular restriction applies such that any means of filtration as ultrafiltration, diafiltration, centrifugation and/or decantation methods may be employed, wherein filtration methods can involve suction and/or pressure filtration steps.

Steps (iv) and/or (v) and/or (vi) can in principle be conducted in any suitable order wherein it is preferred that one or more of said steps is repeated one or more times.

As regards the zeolitic material having a BEA framework structure provided in step (i), as noted in the foregoing, said material is not particularly restricted provided that its framework structure comprises $YO_2$ and $X_2O_3$, wherein Y is a tretravalent element, and X is a trivalent element, and wherein the zeolitic material is obtainable and/or obtained from an organotemplate-free synthetic process. Thus, as concerns the $YO_2: X_2O_3$ molar ratios which the zeolitic material provided in step (i) may display, these are not particularly restricted such that it may display any conceivable $YO_2:X_2O_3$ molar ratio. Preferably, however, the $YO_2: X_2O_3$ molar ratio of the zeolitic material provided in step (i) is comprised in the range of from 1 to 50, more preferably in the range of from 3 to 35, more preferably of from 5 to 25, more preferably of from 6 to 20, more preferably of from 7 to 18, more preferably of from 8 to 15, and more preferably of from 9 to 13. According to the present invention it is particularly preferred that the $YO_2:X_2O_3$ molar ratio of the zeolitic material provided in step (i) is comprised in the range of from 10 to 12.

As regards the tetravalent element Y comprised by the BEA framework structure of the zeolitic material, again, no particular restriction applies such that any suitable tetravalent element Y may be contained in the zeolitic material. Preferably, however, Y comprised in the BEA framework structure of the zeolitic material is selected from the group consisting of Si, Sn, Ti, Zr, Ta, Fe, Ge, and combinations of two or more thereof, and more preferably from the group consisting of Si, Sn, Zr, Ta, Fe, and combinations of two or more thereof, wherein more preferably Y comprises Si and/or Sn, preferably Si and Sn. It is yet further preferred that the tetravalent element Y comprised by the BEA framework structure of the zeolitic material comprises a combination of Si and a further tetravalent element, wherein said further tetravalent element is preferably selected from the group consisting of Sn, Ti, Zr, Ta, Fe, Ge, and combinations of two or more thereof, and more preferably from the group consisting of Sn, Zr, Ta, Fe, and combinations of two or more thereof, wherein more preferably the further tetravalent element is Sn. According to the present invention it is particularly preferred that the tetravalent element Y comprised in the BEA framework structure of the zeolitic material is Si.

Same applies accordingly relative to the trivalent element X comprised in the BEA framework structure of the zeolitic material provided in step (i) such that any suitable one or more trivalent elements may be contained therein. Preferably, the one or more trivalent elements comprised in the BEA framework structure of the zeolitic material is selected from the group consisting of Al, B, In, Ga, and combinations of two or more thereof. According to the inventive method it is particularly preferred that the trivalent element X comprised in the BEA framework structure of the zeolitic material is Al.

Concerning the physical and chemical properties of the zeolitic material having a BEA framework structure provided in step (i) of the inventive method, these are again not particularly restricted such that any conceivable zeolitic material having a BEA framework structure may be employed for obtaining a treated zeolitic material having a BEA framework structure. Thus, as regards the BET surface area of the zeolitic material provided in step (i), in principle any specific surface area may be displayed by the zeolitic material. Thus, by way of example, the BET surface area of the zeolitic material provided in step (i) may range anywhere from 300 to 700 m$^2$/g. Preferably, however, the BET surface area of the zeolitic material provided in step (i) is comprised in the range of from 350 to 650 m$^2$/g, more preferably of from 400 to 575 m$^2$/g, and more preferably of from 425 to 550 m$^2$/g. According to the inventive method it is particularly preferred that the BET surface area of the zeolitic material provided in step (i) ranges from 450 to 500 m$^2$/g. As regards the term "BET surface area" as employed in the present application, it is preferred that said values refer to the BET surface area as determined according to DIN 66135. Furthermore, it is preferred that the values of the BET surface area obtained for the zeolitic material having a BEA framework structure provided in step (i) refers to the surface area obtained from the non-calcined material.

As regards the particular type of zeolitic material having a BEA framework structure which may be employed in step (i) of the inventive method, again no particular restriction applies such that any particular zeolitic material may be employed. According to the present invention it is however particularly preferred that zeolite beta is provided in step (i) as the zeolitic material having a BEA framework structure.

As for the additional workup steps which may be comprised by the inventive method according to particular and preferred embodiments thereof, the sequence of steps (ii) and (iii) may be repeated one or more times. Thus, by way of example, the sequence of steps (ii) and (iii) may be repeated 1 to 5 times, wherein said sequence of steps is preferably repeated 1 to 3 times. According to the present invention it is particularly preferred that in the inventive method the sequence of steps (ii) and (iii) is repeated once or twice.

In addition to relating to a particular method for the preparation of a zeolitic material, the present invention also relates to a zeolitic material having a BEA framework structure which is obtainable and/or obtained according to any of the particular and preferred embodiments of the inventive method as defined in the present application. As noted above, the term "obtainable" refers to any zeolitic material having a BEA framework structure which is either obtained by the method of the present invention as described in any of the particular and preferred embodiments thereof or by any conceivable process which leads to a zeolitic material having a BEA framework structure as may be obtained according to the inventive method.

The present invention, however, also relates to a zeolitic material per se, said zeolitic material having a BEA framework structure having an X-ray diffraction pattern comprising at least the following reflections:

| Intensity (%) | Diffraction angle 2θ/° [Cu K(alpha 1)] |
|---|---|
| [8-46] | [21.49-21.79] |
| 100 | [22.55-22.85] |
| [7-37] | [25.45-25.75] |
| [5-30] | [27.10-27.40] |
| [4-23] | [28.96-29.26] |
| [4-23] | [29.75-30.05] |
| [2-14] | [33.64-33.94] | wherein 100% relates to the intensity of the maximum peak in the X-ray diffraction pattern, and wherein the BEA framework structure comprises YO$_2$ and X$_2$O$_3$, wherein Y is a tetravalent element, and X is a trivalent element.

Preferably, the zeolitic material having a BEA framework structure according to the present invention has an X-ray diffraction pattern comprising at least the following reflections:

| Intensity (%) | Diffraction angle 2θ/° [Cu K(alpha 1)] |
|---|---|
| [13-40] | [21.54-21.74] |
| 100 | [22.60-22.80] |
| [11-33] | [25.50-25.70] |
| [9-27] | [27.15-27.35] |
| [7-20] | [28.01-29.21] |
| [7-20] | [29.80-30.00] |
| [4-12] | [33.69-33.89] | wherein 100% relates to the intensity of the maximum peak in the X-ray diffraction pattern.

According to the present invention it is yet further preferred that the zeolitic material having a BEA framework structure has an X-ray diffraction pattern comprising at least the following reflections:

| Intensity (%) | Diffraction angle 2θ/° [Cu K(alpha 1)] |
|---|---|
| [19-35] | [21.59-21.69] |
| 100 | [22.65-22.75] |
| [15-28] | [25.55-25.65] |
| [12-23] | [27.20-27.30] |
| [9-18] | [28.06-29.16] |
| [9-17] | [29.85-29.95] |
| [6-11] | [33.74-33.84] | wherein 100% relates to the intensity of the maximum peak in the X-ray diffraction pattern.

Preferably, the inventive zeolitic material having a BEA framework structure displaying an X-ray diffraction pattern according to the present invention is a zeolitic material which is either obtained by the inventive method for the preparation of a treated zeolitic material according to any of the particular and preferred embodiments thereof as defined in the present application or by any conceivable process which leads to a zeolitic material having a BEA framework structure as may be obtained i.e. as is obtainable according to the inventive method for the preparation of a treated zeolitic material and in particular according to any of the particular and preferred embodiments thereof as defined in the present application.

As regards the YO$_2$:X$_2$O$_3$ molar ratio of the inventive zeolitic material, no particular restrictions apply such that the inventive zeolitic material having a BEA framework structure may display any conceivable YO$_2$:X$_2$O$_3$ molar ratio. Thus, by way of example, the YO$_2$:X$_2$O$_3$ molar ratio of the zeolitic material having a BEA framework structure may range anywhere from 25 to 600, wherein it is preferred according to the present invention that the YO$_2$:X$_2$O$_3$ molar ratio is comprised in the range of from 50 to 400, more preferably of from 100 to 350, more preferably of from 150 to 300, and more preferably of from 200 to 250. According to the present invention it is particularly preferred that the zeolitic material having a BEA framework structure displays a YO$_2$:X$_2$O$_3$ molar ratio comprised in the range of from 220 to 230.

The zeolitic material of the present invention is preferably characterized by a particular $^{29}$Si MAS NMR spectrum. In particular, as a result of the specific treatment of the zeolitic material having a BEA framework structure obtainable from an organotemplate-free synthetic process as obtainable according to the inventive process, the inventive zeolitic material per se is not only characterized by a specific X-ray diffraction pattern but furthermore displays a particular $^{29}$Si MAS NMR spectrum due to the particular order and high crystallinity of the dealuminated BEA framework compared to zeolitic materials of the BEA framework structure which have been dealuminated according to conventional methods. Thus, it is preferred according to the present invention that the $^{29}$Si MAS NMR spectrum of the inventive zeolitic material according to any of the particular and preferred embodiments as defined in the present application comprises:
one or more peaks (P'1) in the range of from −95 to −104.5 ppm; and
one or more peaks (P'2) in the range of from −105 to −116 ppm;
wherein the ratio of the total integration value of the one or more peaks (P'1) to the one or more peaks (P'2) is comprised in the range of from 19:81 to 35:65.

In this respect, it is noted that according to the present invention there is no particular restriction as to how the $^{29}$Si MAS NMR spectrum of the inventive zeolitic material is obtained wherein preferably the $^{29}$Si MAS NMR spectrum from which the ratio of the total integration value of the one or more peaks (P'1) to the one or more peaks (P'2) is obtained is a deconvoluted $^{29}$Si MAS NMR spectrum. Accordingly, as regards the specific measurement of the $^{29}$Si MAS NMR and the preferred deconvolution of its spectrum, no particular restrictions apply provided that the $^{29}$Si MAS NMR allows for the detection of the peaks and preferably of the deconvoluted peaks. According to the present invention it is preferred that the deconvolution or the peaks in the NMR spectrum and the integration of the peak areas is performed using the program Alice2, Version 6.1 (JEOL). According to the present invention it is however preferred that the measurement of the $^{29}$Si MAS NMR and the deconvolution thereof is performed according to the procedure described in the experimental section of the present application below.

According to the present invention it is further preferred that the $^{29}$Si MAS NMR spectrum of the zeolitic material, and preferably the deconvoluted $^{29}$Si MAS NMR spectrum thereof, comprises:
one or more peaks (P'1) in the range of from −98 to −104 ppm; and
one or more peaks (P'2) in the range of from −106 to −114 ppm;
wherein the ratio of the total integration value of the one or more peaks (P'1) to the one or more peaks (P'2) is comprised in the range of from 21:79 to 33:67.

More preferably, the one or more peaks (P'1) is in the range of from −100 to −103.5 ppm, the one or more peaks (P'2) is in the range of from −107 to −113 ppm, and the ratio of the total integration value of the one or more peaks (P'1) to the one or more peaks (P'2) is comprised in the range of from 23:77 to 31:69. Yet more preferably, the one or more peaks (P'1) is in the range of from −101 to −103 ppm, the one or more peaks (P'2) is in the range of from −107.5 to −112.5 ppm, and the ratio of the total integration value of the aforementioned peaks is comprised in the range of from 25:75 to 29:71. According to the present invention it is particularly preferred that the $^{29}$Si MAS NMR spectrum of the zeolitic material, and preferably the deconvoluted spectrum thereof, comprises: one or more peaks (P'1) in the range of from −101.5 to −102.5 ppm, and one or more peaks (P'2) in the range of from −108 to −112 ppm, wherein the ratio of the total integration value of the one or more peaks (P'1) to the one or more peaks (P'2) is comprised in the range of from 27:73 to 28:72.

In addition to being characterized by a specific $^{29}$Si MAS NMR spectrum, the inventive zeolitic material of the present invention having a BEA framework structure is further characterized by a specific $^{27}$Al MAS NMR spectrum, again, due to the specific structure and substantially intact crystallinity of the zeolitic material as obtainable according to the inventive process, in particular by the calcination treatment compared to the steam treatment methodologies known in the art.

Thus, the present invention further relates to a zeolitic material having a BEA framework structure, wherein the BEA framework structure comprises YO$_2$ and X$_2$O$_3$, wherein Y is a tetravalent element and X is a trivalent element, and wherein the $^{27}$Al MAS NMR of the zeolitic material, comprises:
a first peak (P1) in the range of from 45 to 65 ppm;
a second peak (P2) in the range of from 11 to 44 ppm; and
a third peak (P3) in the range of from −10 to 10 ppm.

Thus, as outlined above relative to the surprising technical effect, it has been found that as compared to a steaming regimen for the dealumination of a zeolitic material as taught in the prior art, the inventive method does not lead to the complete removal of the aluminum species during the calcination treatment but rather leads to a change in the coordination of the aluminum from tetrahedral coordination as observed for framework aluminum to an intermediate coordination tentatively attributed to coordination states in-between the tetravalent coordination and an octahedral coordination as observed for aluminum which has been entirely removed from the zeolitic framework structure, and in particular a pentavalent or pentavalent-like coordination. As a result, the zeolitic materials of the present invention unexpectedly display an intermediate peak (P2) attributed to said intermediate coordination and lying between the typical peaks for aluminum in tetravalent coordination characterized by the first peak (P1) and aluminum in octahedral coordination characterized by the third peak (P3).

Furthermore, as regards the additional peak (P2) observed in the $^{27}$Al MAS NMR spectrum of the inventive zeolitic material, it is preferred that a substantial amount thereof is observed such that it is preferred that the integration of the first, second, and third peaks in the $^{27}$Al MAS NMR of the zeolitic material offers ratios of the integration values P1:P2:P3 comprised in the range of from 1:(0.1-0.8):(0.4-0.9).

As regards the $^{27}$Al MAS NMR of the inventive zeolitic material, there is again no particular restriction according to the present invention as to how said $^{27}$Al MAS NMR is obtained wherein it is however preferred that the $^{27}$Al MAS NMR of the inventive zeolitic material refers to the deconvoluted $^{27}$Al MAS NMR spectrum thereof. Accordingly, as regards the specific measurement of the $^{27}$Al MAS NMR and the preferred deconvolution of its spectrum, no particular restrictions apply provided that the $^{27}$Al MAS NMR allows for the detection of the peaks and preferably of the deconvoluted peaks. According to the present invention it is preferred that the deconvolution or the peaks in the NMR spectrum and the integration of the peak areas is performed using the program Alice2, Version 6.1 (JEOL). According to the present invention it is however preferred that the measurement of the $^{27}$Si MAS NMR and the deconvolution thereof is performed according to the procedure described in the experimental section of the present application below.

Furthermore, although the present invention relates to a zeolitic material having a BEA framework structure characterized by a specific $^{27}$Al MAS NMR per se according to any of the particular and preferred embodiments as defined in the present application, it is nevertheless preferred that said zeolitic material having a BEA framework structure is obtainable and/or obtained according to any of the particular and preferred embodiments of the inventive method for the preparation of a treated zeolitic material as described in any of the particular and preferred embodiments of the present application. It is, however, particularly preferred according to the present invention that the inventive zeolitic material having a BEA framework structure characterized by a particular $^{27}$Al MAS NMR is obtainable and/or obtained according to steps (i) and (ii) of the inventive method for the preparation of a treated zeolitic material according to any of the particular and preferred embodiments of the present application, wherein more preferably the zeolitic material has not been subject to a treatment according to step (iii) according to the inventive method for the preparation of a treated zeolitic material as defined according to any of the particular and preferred embodiments of the present application. Yet more preferably, the inventive zeolitic material having a BEA framework structure characterized by a specific $^{27}$Al MAS NMR spectrum is obtainable and/or obtained directly from step (ii) of the inventive method for the preparation of a treated zeolitic material according to any of the particular and preferred embodiments of the present application, and is preferably a zeolitic material as directly obtained from step (ii) according to any of the particular and preferred embodiments of the present application.

There is no particular restriction according to the present invention as to the standard used in the $^{27}$Al MAS NMR experiments for obtaining the respective values for the chemical shift in ppm in the $^{27}$Al MAS NMR spectra according to particular and preferred embodiments of the present invention, wherein preferably an external standard is used. According to the present invention it is particularly preferred that an aqueous 1 M solution of AlCl$_3$ is used as an external zero reference in the $^{27}$Al MAS NMR experiment for obtaining the $^{27}$Al MAS NMR spectra of the inventive zeolitic material according to any of the particular and preferred embodiments of the present application.

Preferably, the inventive zeolitic material having a BEA framework structure characterized by a specific $^{27}$Al MAS NMR comprises:
a first peak (P1) in the range of from 47 to 63 ppm;
a second peak (P2) in the range of from 16 to 41 ppm and more preferably of from 20 to 39 ppm; and
a third peak (P3) in the range of from −7 to 7 ppm;
wherein preferably the integration of the first, second, and third peaks in the $^{27}$Al MAS NMR of the inventive zeolitic material preferably offers ratios of the integration values P1:P2:P3 comprised in the range of from 1:(0.2-0.75):(0.5-0.85).

More preferably, the inventive zeolitic material having a BEA framework structure displays a $^{27}$Al MAS NMR comprising: a first peak (P1) in the range of from 49 to 61 ppm and preferably from 51 to 59 ppm; a second peak (P2) in the range of from 23 to 37 ppm and preferably of from 25 to 35 ppm; and a third peak (P3) in the range of from −5 to 5 ppm and preferably of from −3 to 3 ppm; wherein preferably the integration values P1:P2. P3 are comprised in the range of from 1:(0.3-0.7):(0.55-0.8) and more preferably of from 1:(0.4-0.65):(0.6-0.75). According to the present invention it is particularly preferred that the zeolitic material having a BEA framework structure displays a $^{27}$Al MAS NMR comprising: a first peak (P1) in the range of from 53 to 57 ppm, and preferably of from 54 to 56 ppm; a second peak (P2) comprised in the range of from 27 to 33 ppm, and preferably from 29 to 31 ppm; and a third peak (P3) in the range of from −2 to 2 ppm, and preferably from −1 to 1 ppm; wherein preferably the integration of the first, second, and third peaks in the $^{27}$Al MAS NMR of the zeolitic material offers ratios of the integration values P1:P2:P3 comprised in the range of from 1:(0.45-0.6):(0.65-0.72), and preferably of from 1:(0.5-0.55):(0.68-0.7).

As regards the YO$_2$:X$_2$O$_3$ molar ratio of the inventive zeolitic material having a BEA framework structure characterized by a specific $^{27}$Al MAS NMR, there is no particular restriction according to the present invention as to the values for said ratio which it may display. Thus, the YO$_2$:X$_2$O$_3$ molar ratio of the inventive zeolitic material characterized by a specific $^{27}$Al MAS NMR spectrum may range anywhere from 3 to 30, wherein preferably the YO$_2$:X$_2$O$_3$ molar ratio ranges from 5 to 20, more preferably from 7 to 15, more preferably from 8 to 13, and more preferably of from 9 to 11. According to the present invention it is particularly preferred that the zeolitic material having a BEA framework structure characterized by a particular $^{27}$Al MAS NMR displays a YO$_2$: X$_2$O$_3$ molar ratio comprised in the range of from 9.5 to 10.5.

The inventive zeolitic materials having a BEA framework structure comprise YO$_2$ in their framework structure wherein Y is a tetravalent element. According to the present invention, there is no particular restriction as to the tetravalent element Y which may be comprised in the BEA framework structure. Thus, by way of example, Y may be selected from the group consisting of Si, Sn, Ti, Zr, Ta, Fe, Ge, and combinations of two or more thereof, and more preferably from the group consisting of Si, Sn, Zr, Ta, Fe, and combinations of two or more thereof, wherein more preferably Y comprises Si and/or Sn, preferably Si and Sn. It is yet further preferred that the tetravalent element Y comprised by the BEA framework structure of the zeolitic material comprises a combination of Si and a further tetravalent element, wherein said further tetravalent element is preferably selected from the group consisting of Sn, Ti, Zr, Ta, Fe, Ge, and combinations of two or more thereof, and more preferably from the group consisting of Sn, Zr, Ta, Fe, and combinations of two or more thereof, wherein more preferably the further tetravalent element is Sn. It is, however, particularly preferred according to the present invention that the tetravalent element Y comprised as YO$_2$ in the BEA framework structure of the inventive zeolitic materials is Si.

The inventive zeolitic materials having a BEA framework structure comprise $X_2O_3$ in their framework structure wherein X is a trivalent element. As regards the trivalent elements which may be contained as X in the framework structure of the inventive zeolitic materials, again no particular restriction applies such that any conceivable trivalent element X may be contained in the BEA framework structure of the inventive zeolitic materials to this effect. It is however preferred according to the present invention that X is selected from the group consisting of Al, B, In, Ga, and combinations of two or more thereof. According to the present invention it is particularly preferred that the trivalent element X comprised as $X_2O_3$ in the inventive zeolitic materials is Al. As regards the further physical and chemical characteristics of the inventive zeolitic materials, these are not particularly restricted. Thus, as regards the BET surface area of the inventive zeolitic materials having a BEA framework structure according to any of the particular and preferred embodiments of the present application, these may display any suitable specific surface area. Thus, by way of example, the BET surface area of the inventive zeolitic materials may range anywhere from 100 to 850 m$^2$/g, wherein preferably the BET surface area is comprised in the range of from 200 to 800 m$^2$/g, more preferably from 300 to 750 m$^2$/g, more preferably from 400 to 720 m$^2$/g, more preferably from 500 to 700 m$^2$/g, and more preferably from 550 to 680 m$^2$/g. According to the present invention it is particularly preferred that the BET surface area of the inventive zeolitic materials is comprised in the range of from 600 to 660 m$^2$/g. Furthermore, as regards the values for the BET surface area as defined in the present application, it is preferred that said values refer to the BET surface area of the inventive zeolitic materials determined according to DIN 66135.

Furthermore, there is no particular restriction as to which particular zeolite may be comprised by the zeolitic materials having a BEA framework structure of the present invention such that any suitable zeolite may be contained therein provided that they display the characteristics of the inventive zeolitic materials as defined in any of the particular and preferred embodiments thereof. It is, however, preferred that the inventive zeolitic materials comprise zeolite beta, wherein even more preferably the inventive zeolitic materials are zeolite beta.

As well as relating to a method for the preparation of a treated zeolitic material having a BEA framework structure and to zeolitic materials per se preferably obtained and/or obtainable according to the inventive method, the present invention also relates to a process for converting oxygenates to olefins. More particularly, the present invention relates to such a process comprising:

(1) providing a gas stream comprising one or more oxygenates;
(2) contacting the gas stream with a catalyst comprising a zeolitic materialaccording to the present invention.

With regard to the catalyst which can be used in the process according to the invention for converting oxygenates to olefins, there is in principle no restriction whatsoever, provided that it comprises a zeolitic material according to the present invention per se or as obtainable according to any of the particular and preferred embodiments of the inventive method for the preparation of a treated zeolitic material having a BEA framework structure, and provided that this catalyst is suitable for the conversion of at least one oxygenate to at least one olefin. This is especially true of the embodiments of the catalyst according to the particular and preferred embodiments of the inventive process.

The same applies correspondingly to the one or more oxygenate(s) present in the gas stream according to (1), and so there is no restriction here whatsoever in principle in the process according to the invention, provided that the one or more oxygenates present in the gas stream according to (1) can be converted by the catalyst comprising the inventive zeolitic material according to the present invention and especially according to the particular and preferred embodiments thereof to at least one olefin when contacted according to (2). According to the present invention, however, it is preferable that the one or more oxygenates present in the gas stream according to (1) are selected from the group consisting of aliphatic alcohols, ethers, carbonyl compounds and mixtures of two or more thereof. Further preferably, the one or more oxygenates are selected from the group consisting of $(C_1-C_6)$-alcohols, di$(C_1-C_3)$alkyl ethers, $(C_1-C_6)$-aldehydes, $(C_2-C_6)$-ketones and mixtures of two or more thereof, further preferably consisting of $(C_1-C_4)$-alcohols, di$(C_1-C_2)$ alkyl ethers, $(C_1-C_4)$-aldehydes, $(C_2-C_4)$-ketones and mixtures of two or more thereof. In yet further preferred embodiments of the present invention, the gas stream according to (1) comprises one or more oxygenates selected from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, the one or more oxygenates further preferably being selected from the group consisting of methanol, ethanol, dimethyl ether, diethyl ether, ethyl methyl ether and mixtures of two or more thereof. In particularly preferred embodiments of the process according to the invention for converting oxygenates to olefins, the gas stream according to (1) comprises methanol and/or dimethyl ether as the one or more oxygenates, and methanol is more preferably the oxygenate present in the gas stream according to (1).

With respect to the manner of contacting the gas stream with a catalyst comprising a zeolitic material according to the present invention in step (2) of the process according to the invention for converting oxygenates to olefins, there is in principle no restriction whatsoever, provided that the conversion of at least one oxygenate to at least one olefin can be implemented. This applies, for example, to the temperature at which the contacting (2) takes place. Thus, for example, the contacting in step (2) of the process according to the invention can take place at a temperature in the range from 200 to 700° C., preference being given to selecting temperatures in the range from 300 to 650° C., further preferably from 350 to 600° C., further preferably from 400 to 575° C. and further preferably from 450 to 550° C. In particularly preferred embodiments of the present invention, the contacting according to (2) of the process according to the invention is performed at a temperature in the range from 475 to 525° C.

In addition, there are no particular restrictions with respect to the manner of performance of the process according to the invention for converting oxygenates to olefins, and so it is possible to use either a continuous or a noncontinuous process, the noncontinuous process being performable, for example, in the form of a batch process. According to the present invention, however, it is preferable to conduct the process according to the invention for the conversion of oxygenates as a continuous process. Thus, according to the present invention, preference is given to embodiments of the process for converting oxygenates to olefins in which the process is a continuous process.

The present invention further also relates to the use of the inventive zeolitic material as described above, and especially to the use of the inventive zeolitic material according to the particular and preferred embodiments as described in the present application. According to the present invention, there is no restriction whatsoever in principle with respect to the use of the inventive zeolitic material, and so it can be used as a catalyst for the conversion of organic compounds, more preferably as a catalyst in a reaction in which one or more carbon-carbon single and/or double bonds, preferably one or more carbon-carbon single bonds, are formed between two carbon atoms which were previously not bound to one another by a carbon-carbon bond. According to the present invention, however, the inventive zeolitic material is preferably used in a methanol-to-olefin process (MTO process), and further preferably in a methanol-to-gasoline process (MTG process), in a methanol-to-hydrocarbon process, in a methanol-to-propylene process (MTP process), in a methanol-to-propylene/butylene process (MT3/4 process) and for alkylation of aromatics, or in a fluid catalytic cracking process (FCC process). According to the present invention, however, the inventive zeolitic material is more preferably used in a methanol-to-olefin process (MTO process). Alternatively, the inventive zeolitic material is preferably used as a catalyst in the treatment of exhaust gas, preferably in selective catalytic reduction (SCR) of $NO_x$ and/or in the abatement of $N_2O$ The present invention is further characterized by the following preferred embodiments, including the combinations of embodiments indicated by the respective dependencies:

1. A method for the preparation of a treated zeolitic material having a BEA framework structure comprising the steps of:
   (i) providing a zeolitic material having a BEA framework structure, wherein the BEA framework structure comprises $YO_2$ and $X_2O_3$, wherein Y is a tetravalent element, and X is a trivalent element, and wherein the zeolitic material having a BEA framework structure is obtainable and/or obtained from an organotemplate-free synthetic process;
   (ii) calcining the zeolitic material provided in step (i) at a temperature of 650° C. or more; and
   (iii) treating the calcined zeolitic material obtained from step (ii) with an aqueous solution having a pH of 5 or less.
2. The method of embodiment 1, wherein the zeolitic material having a BEA framework structure provided in (i) comprises 5 wt.-% or less of one or more non-framework cationic elements other than H+ and/or $NH_4^+$, preferably 3 wt.-% or less, more preferably 2 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less.
3. The method of embodiment 2, wherein the non-framework cationic element is Na or K, wherein preferably the one or more non-framework cationic elements are Na and K, wherein more preferably the one or more non-framework elements are selected from the group consisting of Li, Na, K, and combinations of two or three thereof, more preferably from the group consisting of Li, Na, K, Rb, Cs, and combinations of two or more thereof, more preferably from the group consisting of alkali metals, alkaline earth metals, and combinations of two or more thereof, and more preferably from the group consisting of cationic elements other than H+ and/or $NH_4^+$.
4. The method of any of embodiments 1 to 3, wherein in step (ii) the zeolitic material provided in step (i) is calcined at a temperature comprised in the range of from 680° C. to 1000° C., preferably of from 700° C. to 900° C., more preferably of from 720° C. to 850° C., more preferably of from 750° C. to 830° C., and more preferably of from 790° C. to 810° C.
5. The method of any of embodiments 1 to 4, wherein calcining in step (ii) is conducted for a duration of from 0.5 to 72 h, preferably from 1 to 64 h, more preferably from 2 to 56 h, more preferably from 4 to 48 h, more preferably from 8 to 40 h, more preferably from 12 to 36 h, more preferably from 16 to 32 h, and more preferably from 20 to 28 h.
6. The method of any of embodiments 1 to 5, wherein calcining in step (ii) is conducted in an atmosphere containing 10 wt.-% or less of water, preferably 5 wt.-% or less, preferably 3 wt.-% or less, more preferably 2 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, and more preferably 0.001 wt.-% or less of water.
7. The method of any of embodiments 1 to 6, wherein the pH of the aqueous solution employed in step (iii) is comprised in the range of from −2 to 4, preferably of from −1.8 to 3, more preferably of from −1.6 to 2, more preferably of from −1.4 to 1, more preferably of from −1.2 to 0.5, more preferably of from −1 to 0.2, and more preferably of from −0.8 to 0.
8. The method of any of embodiments 1 to 7, wherein the aqueous solution employed in step (iii) contains 50 wt.-% or more of water based on the total weight of the one or more solvents in the solution, preferably 60 wt.-% or more, more preferably 70 wt.-% or more, more preferably 80 wt.-% or more, more preferably 90 wt.-% or more, more preferably 95 wt.-% or more, more preferably 98 wt.-% or more, more preferably 99 wt.-% or more, more preferably 99.9 wt.-% or more, wherein more preferably water is used as the solvent in the aqueous solution employed in step (iii), preferably distilled water.
9. The method of any of embodiments 1 to 8, wherein the aqueous solution employed in step (iii) contains one or more acids selected from the group consisting of Bronsted acids and Lewis acids, preferably from the group consisting of Bronsted acids, more preferably from the group consisting of inorganic Bronsted acids, wherein more preferably the one or more acids are selected from the group consisting of phosphoric acid, sulphuric acid, hydrochloric acid, nitric acid, and mixtures of two or more thereof, more preferably from the group consisting sulphuric acid, hydrochloric acid, nitric acid, and mixtures of two or more thereof, wherein more preferably the aqueous solution employed in step (iii) contains hydrochloric acid and/or nitric acid, preferably nitric acid, wherein more preferably an aqueous solution of nitric acid is employed in step (iii).
10. The method of any of embodiments 1 to 9, wherein the treatment of the calcined zeolitic material with an aqueous solution having a pH of 5 or less in step (iii) is conducted at a temperature comprised in the range of from 25° C. to the boiling point of the aqueous solution under standard atmospheric pressure, preferably of from 30 to 100° C., preferably of from 40 to 95° C., more preferably of from 50 to 90° C., and even more preferably of from 70 to 80° C.

11. The method of any of embodiments 1 to 10, wherein in step (iii), the weight ratio of the aqueous solution having a pH of 5 or less to the zeolitic material is comprised in the range of from 1 to 500, preferably from 5 to 300, more preferably from 10 to 200, more preferably from 20 to 150, more preferably from 30 to 100, more preferably from 35 to 80, more preferably from 40 to 60, more preferably from 45 to 55.

12. The method of any of embodiments 1 to 11, wherein the treatment of the calcined zeolitic material with an aqueous solution having a pH of 5 or less in step (iii) is conducted for a period of from 0.25 to 48 h, preferably of from 0.5 to 24 h, more preferably of from 1 to 12 h, more preferably of from 1 to 6 h, and even more preferably of from 1.5 to 3.5 h.

13. The method of any of embodiments 1 to 12, wherein the method further comprises the steps of:
    (iv) isolating the zeolitic material obtained in step (iii), preferably by filtration; and/or, preferably and
    (v) optionally washing the zeolitic material obtained in step (iii) or (iv); and/or, preferably and
    (vi) optionally drying the zeolitic material material having a BEA framework structure obtained in steps (iii) or (iv) or (v);
    wherein the steps (iv) and/or (v) and/or (vi) can be conducted in any order, and wherein one or more of said steps is preferably repeated one or more times.

14. The method of any of embodiments 1 to 13, wherein the $YO_2:X_2O_3$ molar ratio of the zeolitic material provided in step (i) is comprised in the range of from 1 to 50, preferably of from 3 to 35, more preferably of from 5 to 25, more preferably of from 6 to 20, more preferably of from 7 to 18, more preferably of from 8 to 15, more preferably of from 9 to 13, and even more preferably in the range of from 10 to 12.

15. The method of any of embodiments 1 to 14, wherein Y is selected from the group consisting of Si, Sn, Ti, Zr, Ta, Fe, Ge, and combinations of two or more thereof, preferably from the group consisting of Si, Sn, Zr, Ta, Fe, and combinations of two or more thereof, wherein more preferably Y comprises Si and/or Sn, preferably Si and Sn, wherein more preferably Y is Si and Sn, Y more preferably being Si.

16. The method of any of embodiments 1 to 15, wherein X is selected from the group consisting of Al, B, In, Ga, and combinations of two or more thereof, X preferably being Al.

17. The method of any of embodiments 1 to 16, wherein the zeolitic material provided in step (i) is non-calcined.

18. The method of any of embodiments 1 to 17, wherein the BET surface area determined according to DIN 66135 of the zeolitic material provided in step (i) ranges from 300 to 700 m²/g, preferably from 350 to 650 m²/g, more preferably from 400 to 575 m²/g, more preferably from 425 to 550 m²/g, and even more preferably from 450 to 500 m²/g, wherein the zeolitic material is preferably non-calcined. [458 m²/g]

19. The method of any of embodiments 1 to 18, wherein the zeolitic material comprise zeolite beta, wherein preferably zeolite beta is employed as the zeolitic material in step (i).

20. The method of any of embodiments 1 to 19, wherein the sequence of steps (ii) and (iii) are repeated one or more times, preferably 1 to 5 times, more preferably 1 to 3 times, and more preferably 1 or 2 times.

21. A zeolitic material having a BEA framework structure obtainable and/or obtained according to a method as defined in any one of embodiments 1 to 20.

22. A zeolitic material having a BEA framework structure, preferably obtainable and/or obtained according to a method as defined in any one of embodiments 1 to 20, having an X-ray diffraction pattern comprising at least the following reflections:

| Intensity (%) | Diffraction angle 2θ/° [Cu K(alpha 1)] |
|---|---|
| [8-46] | [21.49-21.79] |
| 100 | [22.55-22.85] |
| [7-37] | [25.45-25.75] |
| [5-30] | [27.10-27.40] |
| [4-23] | [28.96-29.26] |
| [4-23] | [29.75-30.05] |
| [2-14] | [33.64-33.94] | wherein 100% relates to the intensity of the maximum peak in the X-ray diffraction pattern, and
wherein the BEA framework structure comprises $YO_2$ and $X_2O_3$, wherein Y is a tetravalent element, and X is a trivalent element.

23. The zeolitic material of embodiment 22, wherein the $YO_2:X_2O_3$ molar ratio of the zeolitic material is comprised in the range of from 25 to 600, preferably of from 50 to 400, more preferably of from 100 to 350, more preferably of from 150 to 300, more preferably of from 200 to 250, and even more preferably of from 220 to 230.

24. The zeolitic material of embodiment 22 or 23, wherein the $^{29}Si$ MAS NMR spectrum of the zeolitic material, preferably the deconvoluted $^{29}Si$ MAS NMR spectrum, comprises:
    one or more peaks (P'1) in the range of from −95 to −104.5 ppm, preferably from −98 to −104 ppm, more preferably from −100 to −103.5 ppm, more preferably from −101 to −103 ppm, and more preferably from −101.5 to −102.5 ppm; and
    one or more peaks (P'2) in the range of from −105 to −116 ppm, preferably from −106 to −114 ppm, more preferably from −107 to −113 ppm, more preferably from −107.5 to −112.5 ppm, and more preferably from −108 to −112 ppm;
    wherein the ratio of the total integration value of the one or more peaks (P'1) to the one or more peaks (P'2) is comprised in the range of from 19:81 to 35:65, preferably from 21:79 to 33:67, more preferably from 23:77 to 31:69, more preferably from 25:75 to 29:71, and more preferably from 27:73 to 28:72.

25. A zeolitic material having a BEA framework structure, preferably obtainable and/or obtained according to a method as defined in any one of embodiments 1 to 20, wherein the BEA framework structure comprises $YO_2$ and $X_2O_3$, wherein Y is a tetravalent element, and X is a trivalent element, and wherein the $^{27}Al$ MAS NMR of the zeolitic material, preferably the deconvoluted $^{27}Al$ MAS NMR, comprises:
    a first peak (P1) in the range of from 45 to 65 ppm, preferably from 47 to 63 ppm, more preferably from 49 to 61 ppm, more preferably from 51 to 59 ppm, more preferably from 53 to 57 ppm, and more preferably from 54 to 56 ppm;
    a second peak (P2) in the range of from 11 to 44 ppm, preferably from 16 to 41 ppm, more preferably from 20 to 39 ppm, more preferably from 23 to 37 ppm, more preferably from 25 to 35 ppm, more preferably from 27 to 33 ppm, and more preferably from 29 to 31 ppm; and
    a third peak (P3) in the range of from −10 to 10 ppm, preferably from −7 to 7 ppm, more preferably from −5 to 5 ppm, more preferably from −3 to 3 ppm, more preferably from −2 to 2 ppm, and more preferably from −1 to 1 ppm;
wherein the integration of the first, second, and third peaks in the $^{27}$Al MAS NMR of the zeolitic material offers ratios of the integration values P1:P2:P3 comprised in the range of from 1:(0.1-0.8):(0.4-0.9), preferably of from 1:(0.2-0.75):(0.5-0.85), more preferably of from 1:(0.3-0.7):(0.55-0.8), more preferably of from 1:(0.4-0.65):(0.6-0.75), more preferably of from 1:(0.45-0.6):(0.65-0.72), and more preferably of from 1:(0.5-0.55):(0.68-0.7).

26. The zeolitic material of embodiment 25, wherein the zeolitic material is obtainable and/or obtained according to steps (i) and (ii) of the method according to any of embodiments 1 to 20, wherein preferably the zeolitic material has not been subject to a treatment according to step (iii) according to any of embodiments 1 to 20, wherein more preferably the zeolitic material is a material as directly obtained from step (ii) according to any of embodiments 1 to 20.

27. The zeolitic material of embodiment 25 or 26, wherein the $YO_2:X_2O_3$ molar ratio of the zeolitic material is comprised in the range of from 3 to 30, preferably of from 5 to 20, more preferably of from 7 to 15, more preferably of from 8 to 13, more preferably of from 9 to 11, and even more preferably of from 9.5 to 10.5.

28. The zeolitic material of any of embodiments 22 to 27, wherein Y is selected from the group consisting of Si, Sn, Ti, Zr, Ta, Fe, Ge, and combinations of two or more thereof, preferably from the group consisting of Si, Sn, Zr, Ta, Fe, and combinations of two or more thereof, wherein more preferably Y comprises Si and/or Sn, preferably Si and Sn, wherein more preferably Y is Si and Sn, Y more preferably being Si.

29. The zeolitic material of any of embodiments 22 to 28, wherein X is selected from the group consisting of Al, B, In, Ga, and combinations of two or more thereof, X preferably being Al.

30. The zeolitic material of any of embodiments 22 to 29, wherein the BET surface area of the zeolitic material determined according to DIN 66135 ranges from 100 to 850 m$^2$/g, preferably from 200 to 800 m$^2$/g, more preferably from 300 to 750 m$^2$/g, more preferably from 400 to 720 m$^2$/g, more preferably from 500 to 700 m$^2$/g, more preferably from 550 to 680 m$^2$/g, more preferably from 600 to 660 m$^2$/g.

31. The zeolitic material of any of embodiments 22 to 30, wherein the zeolitic material comprises zeolite beta, wherein preferably the zeolitic material is zeolite beta.

32. A process for converting oxygenates to olefins, comprising:
(1) providing a gas stream comprising one or more oxygenates;
(2) contacting the gas stream with a catalyst comprising a zeolitic material according to any of embodiments 21 to 31.

33. The process of embodiment 32, wherein the gas stream according to (1) comprises one or more oxygenates selected from the group consisting of aliphatic alcohols, ethers, carbonyl compounds and mixtures of two or more thereof, preferably from the group consisting of ($C_1$-$C_6$) alcohols, di($C_1$-$C_3$)alkyl ethers, ($C_1$-$C_6$) aldehydes, ($C_2$-$C_6$) ketones and mixtures of two or more thereof, further preferably consisting of ($C_1$-$C_4$) alcohols, di($C_1$-$C_2$)alkyl ethers, ($C_1$-$C_4$) aldehydes, ($C_2$-$C_4$) ketones and mixtures of two or more thereof, more preferably from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, more preferably from the group consisting of methanol, ethanol, dimethyl ether, diethyl ether, ethyl methyl ether and mixtures of two or more thereof, wherein more preferably the gas stream comprises methanol and/or dimethyl ether as the one or more oxygenates, preferably methanol.

34. The process of embodiment 32 or 33, wherein the contacting according to (2) is effected at a temperature in the range from 200 to 700° C., preferably from 300 to 650° C., further preferably from 350 to 600° C., further preferably from 400 to 575° C., further preferably from 450 to 550° C., and further preferably from 475 to 525° C.

35. The process of any of embodiments 32 to 34, wherein the process is a continuous process.

36. Use of a zeolitic material having a BEA framework structure according to any of embodiments 21 to 31 as a catalyst, preferably as a catalyst for the conversion of organic compounds, more preferably as a catalyst in a reaction in which one or more carbon-carbon single and/or double bonds, preferably one or more carbon-carbon single bonds, are formed between two carbon atoms which were previously not bound to one another by a carbon-carbon bond, more preferably in a methanol-to-olefin process (MTO process), in a methanol-to-gasoline process (MTG process), in a methanol-to-hydrocarbon process, in a methanol-to-propylene process (MTP process), in a methanol-to-propylene/butylene process (MT3/4 process), for alkylation of aromatics or in fluid catalytic cracking processes (FCC processes).

37. Use according to embodiment 36, wherein the zeolitic material having a BEA framework structure according to any of embodiments 21 to 31 is used as a catalyst in the treatment of exhaust gas, preferably in selective catalytic reduction (SCR) of $NO_x$ and/or in the abatement of $N_2O$.

EXPERIMENTAL SECTION

Figure 1:
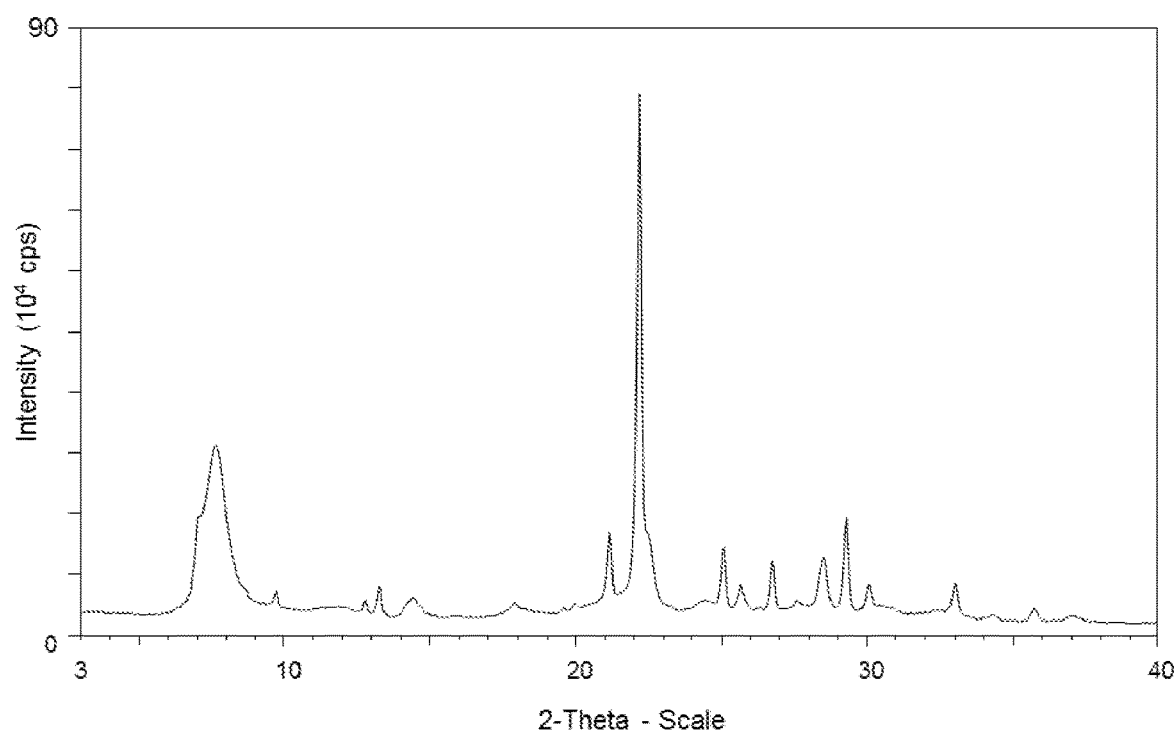
FIGS. 1, 2a, 3a, 4a, 5a, 6a, 7a, 8a, 9a, 10a, 11a, 12a, 13a, 14a, 15a, and 16a respectively display the X-ray diffractions pattern using the samples from Reference Examples 1-5, Examples 6-14, and Comparative Examples 15 and 16 which was measured with a wavelength of 1.54060 Å. The abscissa axis represents the reflection angle "2-Theta" or "2θ" in ° 2theta, and the ordinate axis the measured intensity in the dimensionless unit "counts".

Powder XRD patterns were collected on a Rint-Ultima III (Rigaku) using a Cu Kα X-ray source (40 kV, 20 mA). Sample preparation for XRD was done by typical method using slide glass. First, sample was well grained using a mortar. Then it was put on slide glass, and it was pressed flat with a slide glass.

$^{27}$Al MAS NMR: Solid-state $^{27}$Al MAS NMR spectra of these samples were recorded on a JEOL ECA-600 spectrometer at a resonance frequency of 156.4 MHz using a 4 mm sample rotor with a spinning rate of 15.0 kHz. The spectra were recorded with single-pulse acquisition at ambient temperature using π/2 pulse and a recycle delay of 0.5 s and accumulating 2000 scans. For $^{27}$Al MAS NMR, Chemical shifts were referenced relative to an aqueous Al(NO$_3$)$_3$ solution. To deconvolute the spectra and integrate the peak areas, Alice2 Ver. 6.1 (JEOL) was used.

$^{29}$Si MAS NMR: Solid-state $^{29}$Si MAS NMR spectra were measured on a JEOL ECA-400 spectrometer at a resonance frequency of 79.5 MHz using a 6 mm sample rotor with a spinning rate of 5.5 kHz. The spectra were recorded with single-pulse acquisition at ambient temperature using π/2 pulse and a recycle delay of 60 s and accumulating 1000 scans. The calcined samples were allowed to be cooled to ambient temperature and then stored in glass vessel. The acid-treated samples were dried overnight and stored in the same way. These samples were not further treated prior to the measurement of NMR spectra. For $^{29}$Si MAS NMR, Chemical shifts were referenced relative to tetramethylsilane. To deconvolute the spectra and integrate the peak areas, Alice2 Ver. 6.1 (JEOL) was used.

REFERENCE EXAMPLE 1: Organotemplate-Free Synthesis of Zeolite Beta 335.1 g of NaAlO$_2$ were dissolved in 7314 g of H$_2$O while stirring, followed by addition of 74.5 g of zeolite Beta seeds (commercially obtained from Zeolyst International, product name: CP814C. Prior to the synthesis, the product was calcined at 500° C. for 5 h (heating ramp 1° C./min to obtain the H-Form)). The mixture was placed in a 20 L autoclave together with 7340 g sodium waterglass and 1436 g Ludox AS40, affording an aluminosilicate gel with a molar ratio of 1.00 SiO$_2$:0.042 Al$_2$O$_3$:0.57 Na$_2$O:17.5 H$_2$O. Crystallization took place at 120° C. for 117 h. After the reaction mixture was cooled down to room temperature, the solid was separated by filtration, repeatedly washed with distilled water and then dried at 120° C. for 16 h affording 1337 g of a white crystalline product. Chemical analysis indicated an SiO$_2$:Al$_2$O$_3$ molar ratio of 10.89 and 6.7 wt-% of Na$_2$O on a calcined basis.

1000 g sodium form of the crystalline product was added into 10,000 g of a 10 wt % solution of ammonium nitrate. The suspension was heated to 80° C. and kept at this temperature under continuous stirring for 2 h. The solid was filtered hot (without additional cooling) over a filter press. The filter cake then was then washed with distilled water (room temperature wash water) until the conductivity of the wash water was below 200 μS cm$^{-1}$. The filter cake was dried for 16 h at 120° C. This procedure was repeated once, affording the ion-exchanged crystalline product in its ammonium form. Chemical analysis indicated an SiO$_2$:Al$_2$O$_3$ molar ratio of 10.51 and 6.7 wt-% of Na$_2$O on a calcined basis.

The following values obtained from the X-ray diffractogram (cf. FIG. 1) indicated that a BEA-type framework structure has been obtained.

| Angle [2-Theta °] | Intensity [%] |
|---|---|
| 6.475 | 6 |
| 7.058 | 22.1 |
| 7.616 | 35.3 |
| 9.7 | 7.8 |
| 11.776 | 5 |
| 12.743 | 6.5 |
| 13.247 | 8.9 |
| 14.42 | 6.7 |
| 17.895 | 5.6 |
| 19.599 | 5 |
| 20.021 | 5.8 |
| 21.152 | 18.7 |
| 22.207 | 100 |
| 22.488 | 18.6 |
| 24.471 | 6.3 |
| 25.093 | 16.1 |
| 25.672 | 9 |
| 26.309 | 5.2 |
| 26.771 | 13.6 |
| 27.593 | 6.3 |
| 28.525 | 14.2 |
| 29.297 | 21.5 |
| 30.136 | 9.3 |
| 30.543 | 5.4 |
| 30.911 | 5 |
| 33.055 | 9.4 |

To convert the NH$_4$-form into H-form, the sample was treated by a calcination step at 500° C. for 5 h (heat ramp 1° C./min). Chemical analysis indicated an Si/Al molar ratio of 5.0 and <0.1 wt-% of Na$_2$O on a calcined basis.

$^{27}$Al MAS NMR analysis revealed the following signal intensities in %: 50-60 ppm (Tetra-coordinated Al-sites) 100.0%, 15-45 ppm (Penta-coordinated Al-sites) 0.0%, −10-10 ppm (Hexa-coordinated Al-sites) 0.0%.

REFERENCE EXAMPLE 2: Calcination of Zeolite Beta at 800° C. for 24 h

For calcination, the NH$_4$-form of zeolite beta obtained in Reference Example 1 was taken as starting material. The white powder was heated in a muffle furnace with 3K/min to 800° C. under air. The temperature was held constant for 24 h. Afterwards, the sample was cooled down to room temperature. Chemical analysis indicated an Si/Al molar ratio of 5.0 and <0.1 wt-% of Na$_2$O on a calcined basis.

Figure 2A:
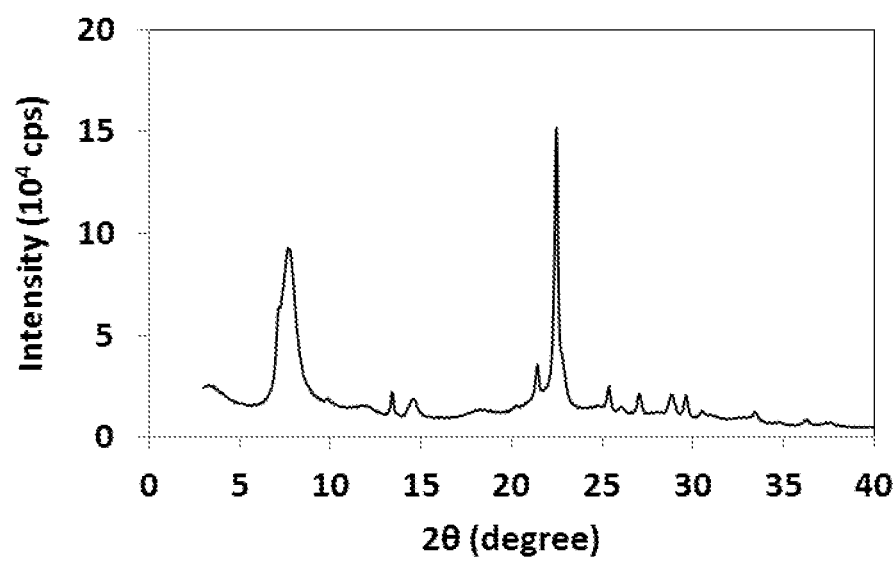
Figure 2B:
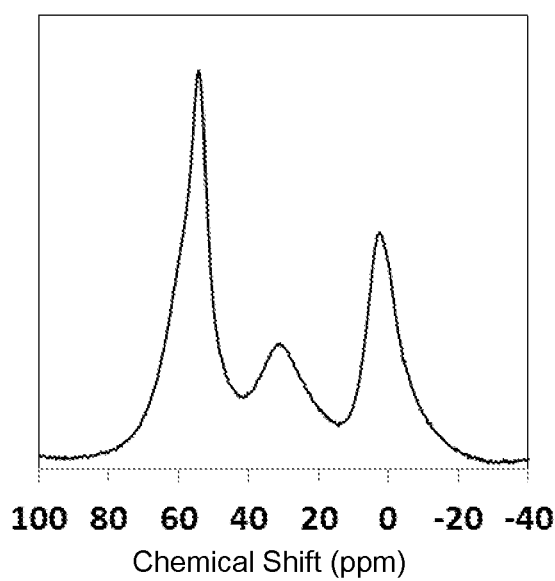
FIGS. 2b, 3b, 4b, and 5b respectively display the $^{27}$Al MAS NMR spectra obtained using the samples from Reference Examples 2-5. In the figures, the values in ppm are plotted along the abscissa, and the signal intensity in arbitrary units is plotted along the ordinate, respectively.
Figure 2C:
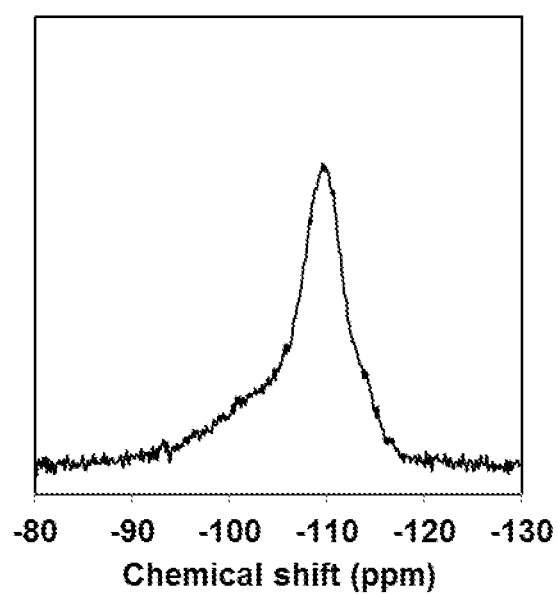
FIGS. 2c, 3c, 4c, 5c, 6b, 7b, 8b, 9b, 10b, 11 b, 12b, 13b, 14b, 15b, and 16b respectively display the $^{29}$Si MAS NMR spectra obtained using the samples from Reference Examples 2-5, Examples 6-14, and Comparative Examples 15 and 16. In the figures, the values in ppm are plotted along the abscissa, and the signal intensity in arbitrary units is plotted along the ordinate, respectively.

The X-ray diffraction pattern of the sample obtained is displayed in FIG. 2a. The BET surface area was measured by means of nitrogen sorption at 77K and afforded a value of 611 m$^2$/g. $^{27}$Al MAS NMR analysis (cf. FIG. 2b) revealed the following signal intensities in %: 50-60 ppm (Tetra-coordinated Al-sites) 45.3%, 15-45 ppm (Penta-coordinated Al-sites) 23.5%, −10-10 ppm (Hexa-coordinated Al-sites) 31.1%. The $^{29}$Si MAS NMR of the sample obtained is displayed in FIG. 2c and revels the following signal intensities in %: −102 ppm (Q4 (1Al)+Q3) 26%, 15-108 ppm (Q4 (0Al, T3-T9)) 61%, −112 ppm (Q4 (0Al, T1-T2)) 9%.

REFERENCE EXAMPLE 3: Calcination of Zeolite Beta at 750° C. for 15 h

For calcination, the NH$_4$-form of zeolite beta obtained in Reference Example 1 was taken as starting material. The white powder was heated in a muffle furnace with 3K/min to 750° C. under air. The temperature was held constant for 15 h. Afterwards, the sample was cooled down to room temperature. Chemical analysis indicated a Si/Al ratio of 5.0 and <0.1 wt-% of $Na_2O$ on a calcined basis. The BET surface area was measured by means of nitrogen sorption at 77K affording a value of 604 $m^2/g$.

Figure 3A:
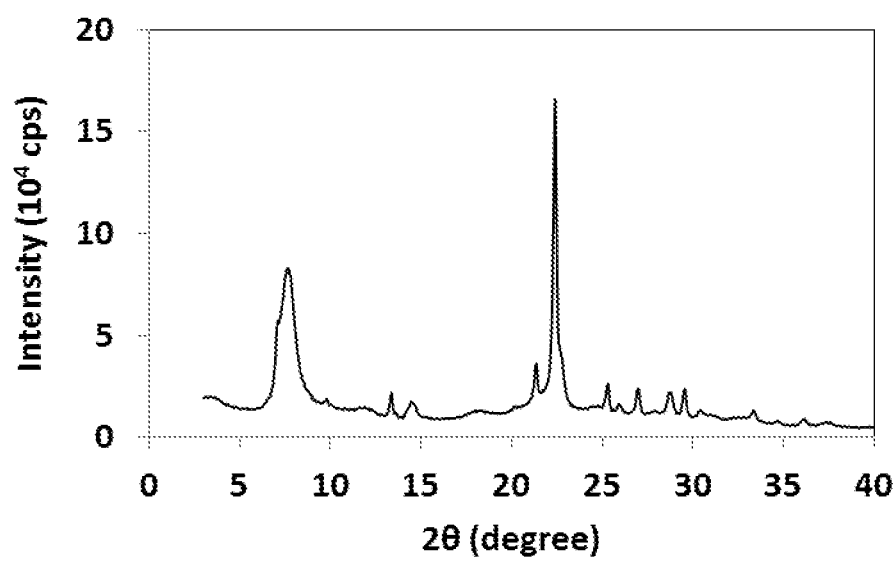

The X-ray diffraction pattern of the sample obtained is displayed in FIG. 3a, and displays the following reflections and corresponding intensities:

| Angle [2-Theta °] | Intensity [%] |
|---|---|
| 3.39 | 12.2 |
| 6.603 | 12 |
| 7.134 | 34.3 |
| 7.694 | 50.8 |
| 9.817 | 11.7 |
| 11.782 | 8.7 |
| 13.346 | 13.4 |
| 13.57 | 7.4 |
| 14.508 | 10.5 |
| 18.202 | 8.1 |
| 20.154 | 9.5 |
| 21.345 | 22.1 |
| 21.703 | 14.3 |
| 22.4 | 100 |
| 22.641 | 27.1 |
| 24.435 | 9.2 |
| 24.762 | 9.4 |
| 25.297 | 16 |
| 25.966 | 10 |
| 26.948 | 14.4 |
| 27.93 | 8 |
| 28.643 | 13.6 |
| 29.297 | 34.7 |
| 29.536 | 14.2 |
| 30.413 | 8.1 |
| 30.83 | 6.9 |
| 32.465 | 6 |
| 33.358 | 8.2 |
| 36.124 | 5.6 |

Figure 3B:
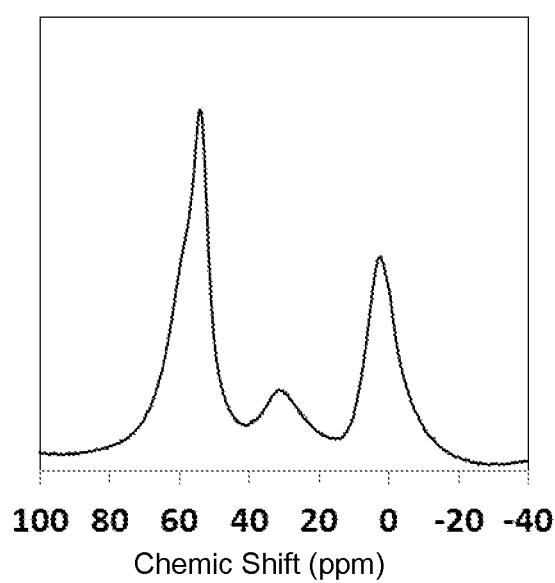
Figure 3C:
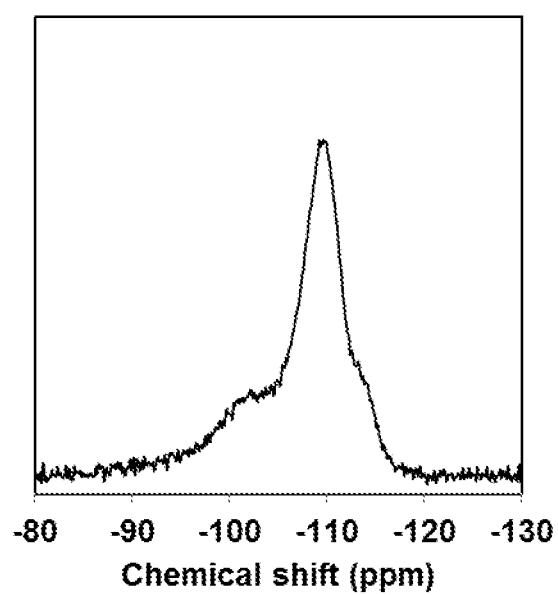

$^{27}Al$ MAS NMR analysis (see FIG. 3b) revealed the following signal intensities in %: 50-60 ppm (Tetra-coordinated Al-sites) 50.7%, 15-45 ppm (Penta-coordinated Al-sites) 16.1%, −10-10 ppm (Hexa-coordinated Al-sites) 33.1%. The $^{29}Si$ MAS NMR of the sample obtained is displayed in FIG. 3c and revels the following signal intensities in %: −102 ppm (Q4 (1Al)+Q3) 26%, 15-108 ppm (Q4 (0Al, T3-T9)) 63%, −112 ppm (Q4 (0Al, T1-T2)) 8%.

REFERENCE EXAMPLE 4: Calcination of Zeolite Beta at 750° C. for 5 h

For calcination, the $NH_4$-form of zeolite beta obtained in Reference Example 1 was taken as starting material. The white powder was heated in a muffle furnace with 3K/min to 750° C. under air. The temperature was held constant for 5 h. Afterwards, the sample was cooled down to room temperature. Chemical analysis indicated an Si/Al molar ratio of 5.0 and <0.1 wt-% of $Na_2O$ on a calcined basis. The BET surface area was measured by means of nitrogen sorption at 77K afforded a value of 644 $m^2/g$.

Figure 4A:
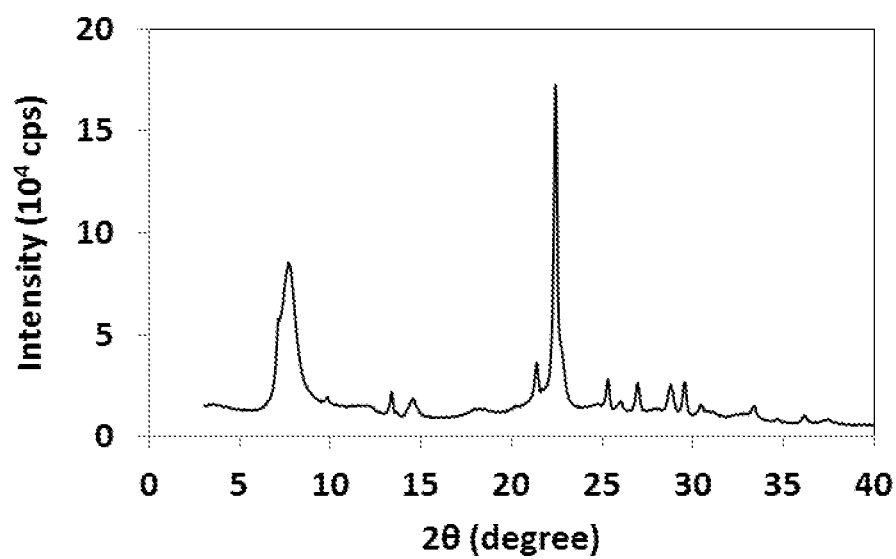

The X-ray diffraction pattern of the sample obtained is displayed in FIG. 4a, and displays the following reflections and corresponding intensities:

| Angle [2-Theta °] | Intensity [%] |
|---|---|
| 7.155 | 34.1 |
| 7.714 | 49.6 |
| 9.826 | 11.5 |
| 11.952 | 9.2 |
| 13.383 | 12.6 |
| 13.669 | 7.5 |
| 14.364 | 9.6 |
| 14.514 | 10.8 |
| 15.414 | 6 |
| 18.235 | 8.1 |
| 20.224 | 9 |
| 21.383 | 20.8 |
| 21.692 | 13.6 |
| 22.406 | 100 |
| 22.66 | 27.8 |
| 24.708 | 9.4 |
| 25.299 | 16.4 |
| 25.991 | 10 |
| 26.958 | 15.3 |
| 27.903 | 8.1 |
| 28.747 | 14.8 |
| 29.535 | 15.6 |
| 30.424 | 8.9 |
| 30.93 | 7.2 |
| 32.651 | 6.6 |
| 33.394 | 8.9 |
| 34.677 | 5.2 |
| 36.162 | 6.1 |

Figure 4B:
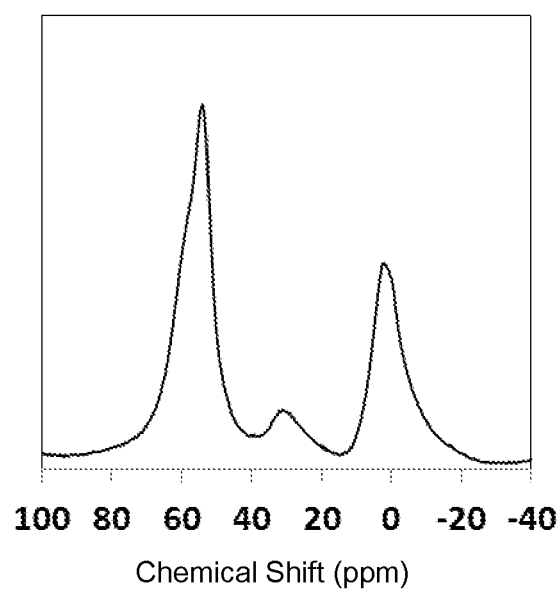
Figure 4C:
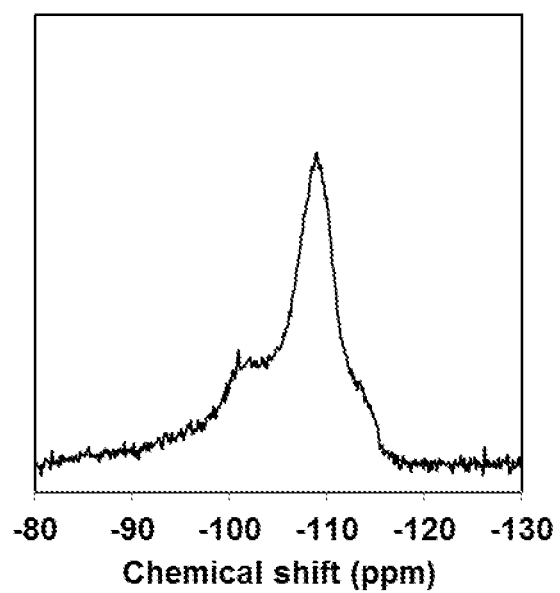

$^{27}Al$ MAS NMR analysis (see FIG. 4b) revealed the following signal intensities in %: 50-60 ppm (Tetra-coordinated Al-sites) 56.5%, 15-45 ppm (Penta-coordinated Al-sites) 9.9%, −10 10 ppm (Hexa-coordinated Al-sites) 33.5%. The $^{29}Si$ MAS NMR of the sample obtained is displayed in FIG. 4c and revels the following signal intensities in %: −102 ppm (Q4 (1Al)+Q3) 26%, 15-108 ppm (Q4 (0Al, T3-T9)) 56%, −112 ppm (Q4 (0Al, T1-T2)) 7%.

REFERENCE EXAMPLE 5: Calcination of Zeolite Beta at 700° C. for 5 h

For calcination, the $NH_4$-form of zeolite beta obtained in Reference Example 1 was taken as starting material. The white powder was heated in a muffle furnace with 3K/min to 700° C. under air. The temperature was held constant for 5 h. Afterwards, the sample was cooled down to room temperature. Chemical analysis indicated an Si/Al molar ratio of 5.0 and <0.1 wt-% of $Na_2O$ on a calcined basis. The BET surface area was measured by means of nitrogen sorption at 77K and afforded a value of 660 $m^2/g$.

Figure 5A:
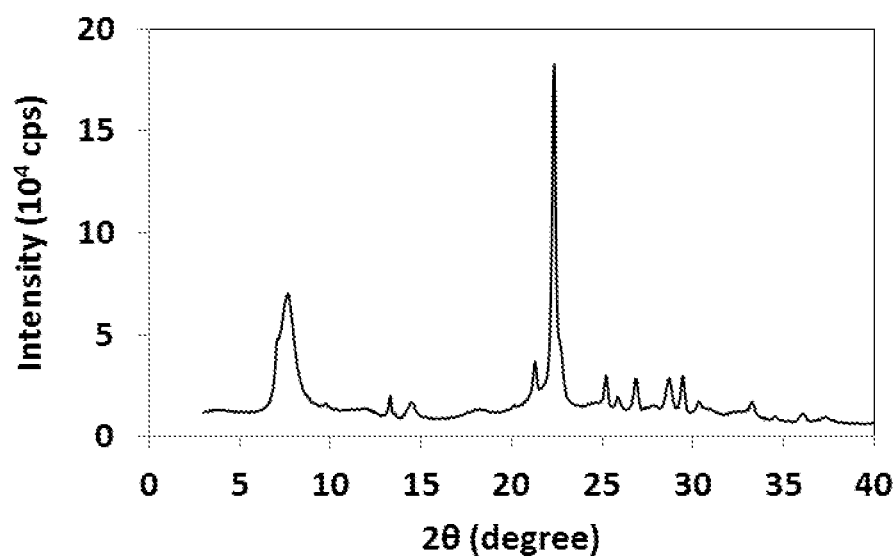

The X-ray diffraction pattern of the sample obtained is displayed in FIG. 5a, and displays the following reflections and corresponding intensities:

| Angle [2-Theta °] | Intensity [%] |
|---|---|
| 7.065 | 26.4 |
| 7.65 | 38.7 |
| 9.745 | 9 |
| 11.856 | 7.7 |
| 13.302 | 10.8 |
| 13.562 | 6.3 |
| 14.487 | 9.4 |
| 18.077 | 7.5 |
| 20.172 | 8.7 |
| 21.293 | 20.2 |
| 22.346 | 100 |
| 22.592 | 26.7 |
| 24.451 | 9.2 |

-continued

| Angle<br>[2-Theta °] | Intensity<br>[%] |
|---|---|
| 25.198 | 16.2 |
| 25.853 | 10.7 |
| 26.848 | 15.9 |
| 27.774 | 8.5 |
| 28.689 | 15.6 |
| 29.405 | 16.2 |
| 30.35 | 9.3 |
| 30.777 | 7.8 |
| 32.439 | 7.1 |
| 33.277 | 9.6 |
| 34.542 | 5.4 |
| 36.082 | 6.3 |
| 37.317 | 5.4 |

Figure 5B:
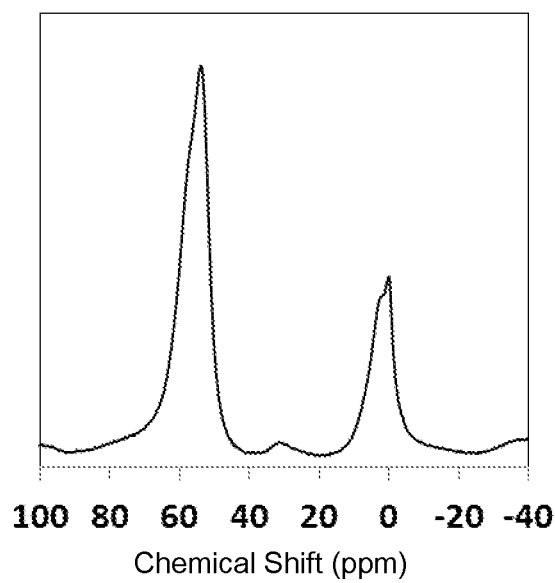
Figure 5C:
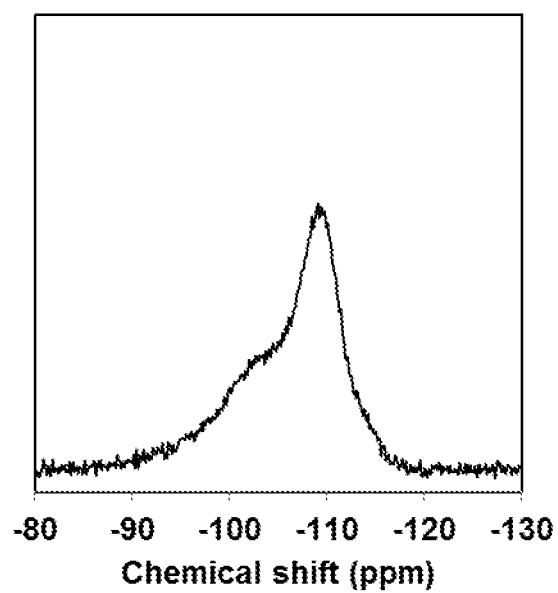

$^{27}$Al MAS NMR analysis (see FIG. 5b) revealed the following signal intensities in %: 50-60 ppm (Tetra-coordinated Al-sites) 71.9%, 15-45 ppm (Penta-coordinated Al-sites) 1.2%, −10 10 ppm (Hexa-coordinated Al-sites) 26.9%. The $^{29}$Si MAS NMR of the sample obtained is displayed in FIG. 5c and revels the following signal intensities in %: −102 ppm (Q4 (1Al)+Q3) 36%, 15-108 ppm (Q4 (0Al, T3-T9)) 49%, −112 ppm (Q4 (0Al, T1-T2)) 7%.

EXAMPLE 6: Acid Treatment (1M) of Calcined Zeolite Beta (700° C./5 h) for 24 h at Ambient Temperature The calcined sample obtained from Reference Example 5 was taken as starting material. 1 g of the white powder was dispersed in 50 ml 1 M nitric acid solution in H$_2$O and stirred in a round bottom flask at 25° C. for 24 hours. Afterwards the solid was extracted by vacuum filtration and subsequent washing with deionized H$_2$O until a pH of 7 was reached. Finally the obtained white powder was dried for 12 hours at 100° C. under air in a muffle furnace. Chemical analysis indicated an Si/Al molar ratio of 75 and <0.1 wt-% of Na$_2$O on a calcined basis. The BET surface area was measured by means of nitrogen sorption at 77K afforded a value of 386 m$^2$/g.

Figure 6A:
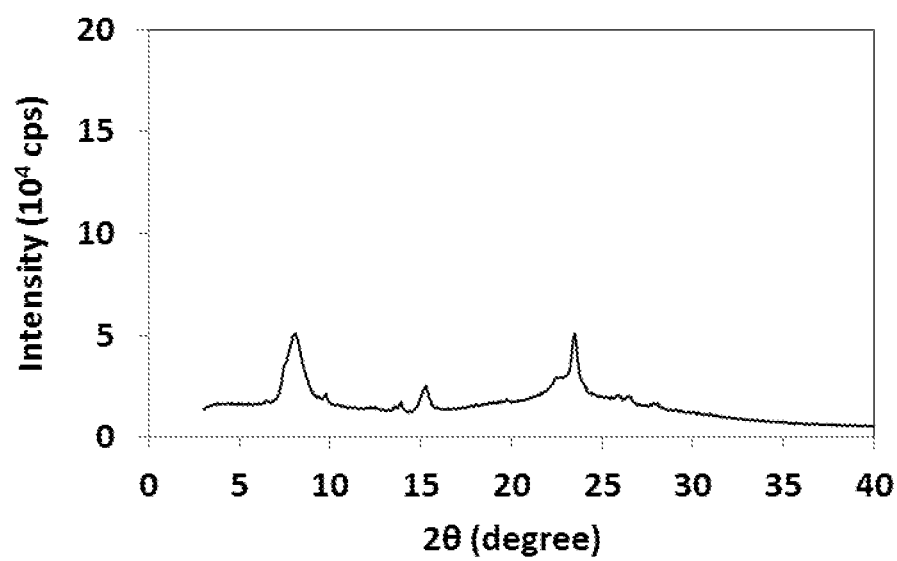

The X-ray diffraction pattern of the sample obtained is displayed in FIG. 6a, and displays the following reflections and corresponding intensities:

| Angle<br>[2-Theta °] | Intensity<br>[%] |
|---|---|
| 7.065 | 26.4 |
| 7.65 | 38.7 |
| 9.745 | 9 |
| 11.856 | 7.7 |
| 13.302 | 10.8 |
| 13.562 | 6.3 |
| 14.487 | 9.4 |
| 18.077 | 7.5 |
| 20.172 | 8.7 |
| 21.293 | 20.2 |
| 22.346 | 100 |
| 22.592 | 26.7 |
| 24.451 | 9.2 |
| 25.198 | 16.2 |
| 25.853 | 10.7 |
| 26.848 | 15.9 |
| 27.774 | 8.5 |
| 28.689 | 15.6 |
| 29.405 | 16.2 |
| 30.35 | 9.3 |
| 30.777 | 7.8 |
| 32.439 | 7.1 |
| 33.277 | 9.6 |
| 34.542 | 5.4 |
| 36.082 | 6.3 |
| 37.317 | 5.4 |

Figure 6B:
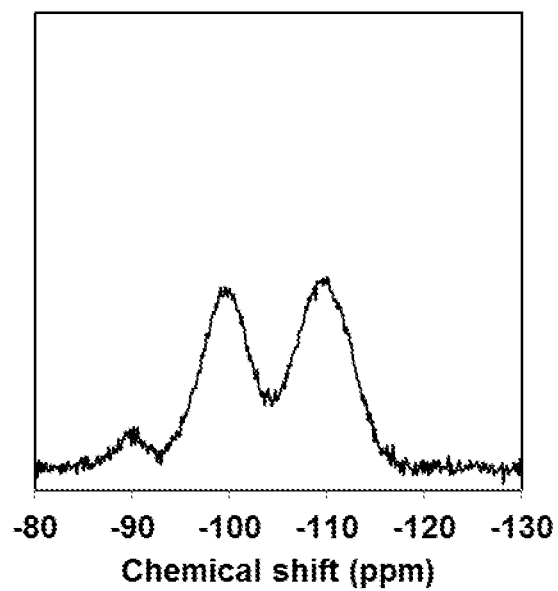

The $^{29}$Si MAS NMR of the sample obtained is displayed in FIG. 6b and revels the following signal intensities in %: −102 ppm (Q4 (1Al)+Q3) 44%, 15-108 ppm (Q4 (0Al, T3-T9)) 38%, −112 ppm (Q4 (0Al, T1-T2)) 13%.

EXAMPLE 7: Acid Treatment (1 M) of Calcined Zeolite Beta (750° C./15 h) for 2 h Under Reflux The calcined sample obtained from Reference Example 3 was taken as starting material. 1 g of the white powder was dispersed in 50 ml 1 M nitric acid solution in H$_2$O and stirred in a round bottom flask at 100° C. under reflux for 2 hours. Afterwards the solid was extracted by vacuum filtration and subsequent washing with DI H$_2$O until a pH of 7 was reached. Finally the obtained white powder was dried for 12 hours at 100° C. under air in a muffle furnace. Chemical analysis indicated a Si/Al ratio of 98 and <0.1 wt-% of Na$_2$O on a calcined basis. The BET surface area was measured by means of nitrogen sorption at 77K of 571 m$^2$/g.

Figure 7A:
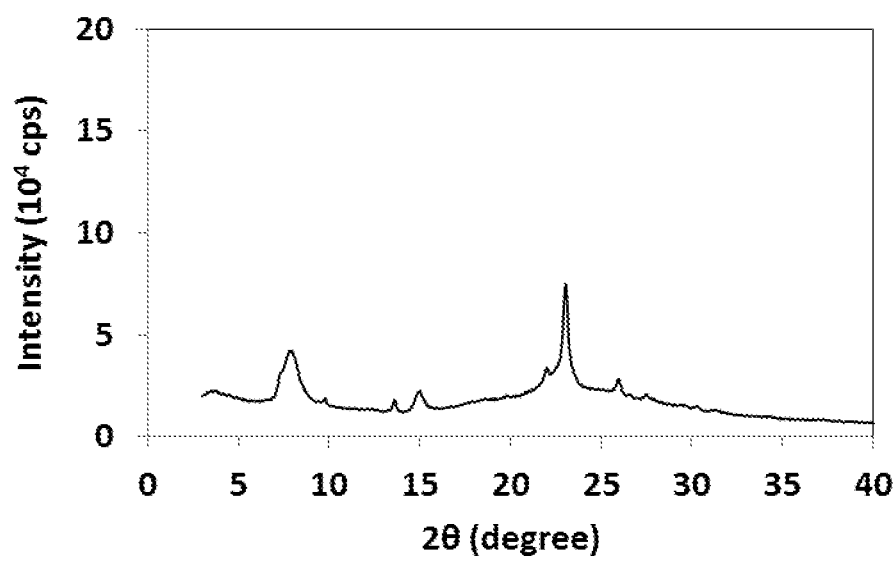

The X-ray diffraction pattern of the sample obtained is displayed in FIG. 7a, and displays the following reflections and corresponding intensities:

| Angle<br>[2-Theta °] | Intensity<br>[%] |
|---|---|
| 3.613 | 30.1 |
| 7.311 | 42.1 |
| 7.9 | 56.7 |
| 9.757 | 25.1 |
| 13.601 | 23.9 |
| 14.965 | 30.2 |
| 18.624 | 24.9 |
| 19.791 | 27.2 |
| 22 | 44.9 |
| 23.05 | 100 |
| 25.951 | 37.7 |
| 26.545 | 27.5 |
| 27.332 | 26.5 |
| 27.492 | 28.2 |
| 29.5 | 20.8 |
| 30.271 | 20 |
| 31.234 | 17.7 |
| 34.301 | 13.8 |

Figure 7B:
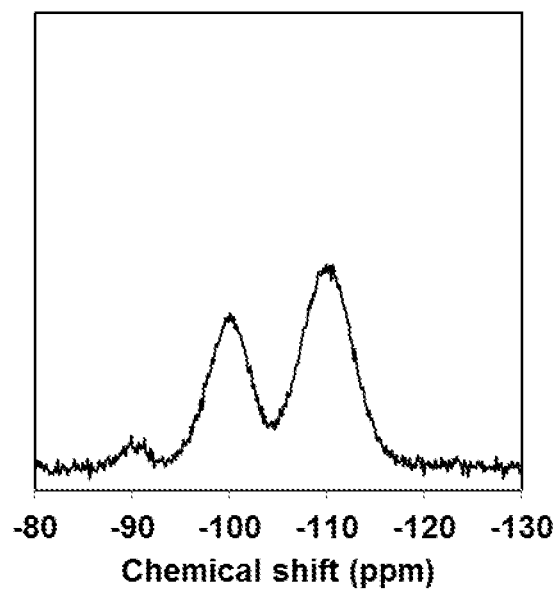

The $^{29}$Si MAS NMR of the sample obtained is displayed in FIG. 7b and revels the following signal intensities in %: −102 ppm (Q4 (1Al)+Q3) 36%, 15-108 ppm (Q4 (0Al, T3-T9)) 42%, −112 ppm (Q4 (0Al, T1-T2)) 19%.

EXAMPLE 8: Acid Treatment (6M) of Zeolite Beta (750° C./5 h) for 24 h Under Reflux The calcined sample obtained from Reference Example 4 was taken as starting material. 1 g of the white powder was dispersed in 50 ml 6 M nitric acid solution in H$_2$O and stirred in a round bottom flask at 100° C. under reflux for 24 hours. Afterwards the solid was extracted by vacuum filtration and subsequent washing with deionized H$_2$O until a pH of 7 was reached. Finally the obtained white powder was dried for 12 hours at 100° C. under air in a muffle furnace. Chemical analysis indicated an Si/Al molar ratio of 227 and <0.1 wt-% of $Na_2O$ on a calcined basis. The BET surface area was measured by means of nitrogen sorption at 77K afforded a value of 495 m²/g.

Figure 8A:
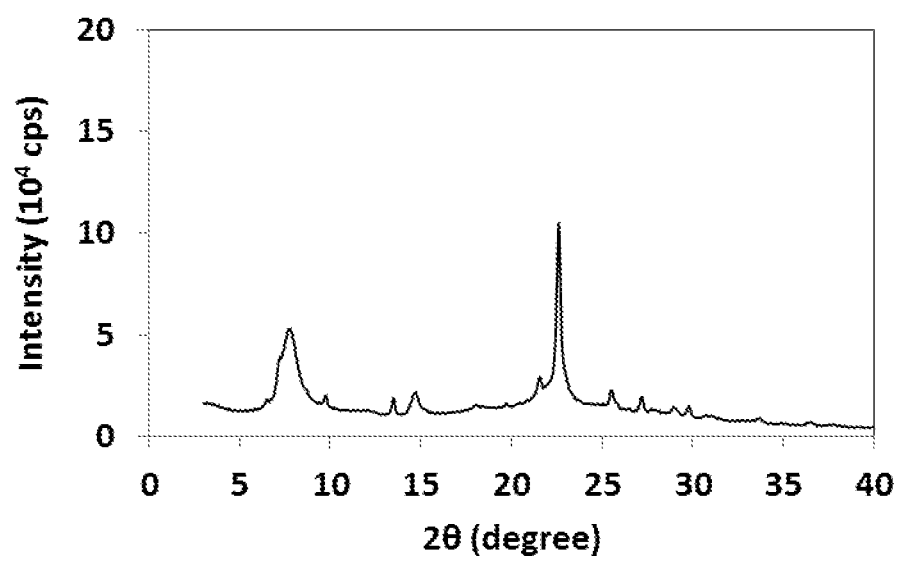

The X-ray diffraction pattern of the sample obtained is displayed in FIG. 8a, and displays the following reflections and corresponding intensities:

| Angle [2-Theta °] | Intensity [%] |
|---|---|
| 6.542 | 17.8 |
| 7.205 | 37.6 |
| 7.771 | 50.4 |
| 8.676 | 22.2 |
| 9.746 | 19.2 |
| 11.992 | 12.5 |
| 13.499 | 18.4 |
| 14.377 | 14.3 |
| 14.675 | 20.9 |
| 15.256 | 12.8 |
| 18.072 | 14.7 |
| 19.74 | 15.6 |
| 21.573 | 28.1 |
| 22.601 | 100 |
| 22.66 | 45.6 |
| 25.551 | 21.8 |
| 26.534 | 13.5 |
| 27.16 | 18.7 |
| 27.8 | 12.8 |
| 28.948 | 14.2 |
| 29.812 | 14.5 |
| 30.72 | 10.3 |
| 31.123 | 9.6 |
| 33.655 | 8.5 |
| 34.952 | 6.6 |
| 36.501 | 6.8 |
| 37.708 | 5.7 |

Figure 8B:
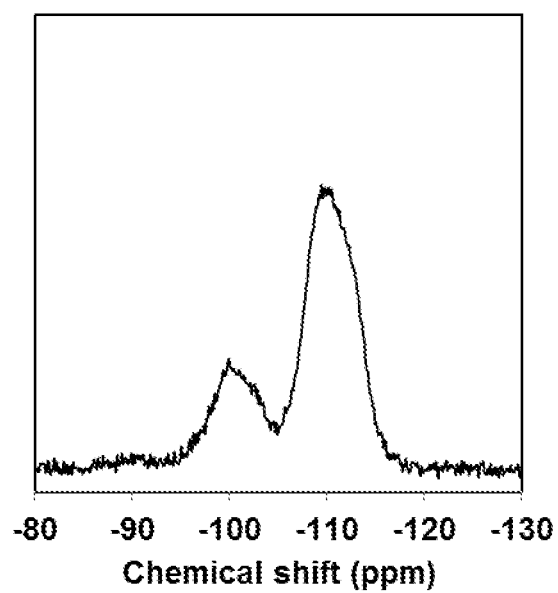

The $^{29}$Si MAS NMR of the sample obtained is displayed in FIG. 8b, and revels the following signal intensities in %: −102 ppm (Q4 (1Al)+Q3) 24%, 15-108 ppm (Q4 (0Al, T3-T9)) 52%, −112 ppm (Q4 (0Al, T1-T2)) 21%.

EXAMPLE 9: Acid Treatment (6M) of Zeolite Beta (700° C./5 h) for 24 h Under Reflux The calcined sample obtained from Reference Example 5 was taken as starting material. 1 g of the white powder was dispersed in 50 ml 6 M nitric acid solution in $H_2O$ and stirred in a round bottom flask at 100° C. under reflux for 24 hours. Afterwards the solid was extracted by vacuum filtration and subsequent washing with deionized $H_2O$ until a pH of 7 was reached. Finally the obtained white powder was dried for 12 hours at 100° C. under air in a muffle furnace. Chemical analysis indicated a Si/Al ratio of 316 and <0.1 wt-% of $Na_2O$ on a calcined basis. The BET surface area was measured by means of nitrogen sorption at 77K afforded a value of 362 m²/g.

Figure 9A:
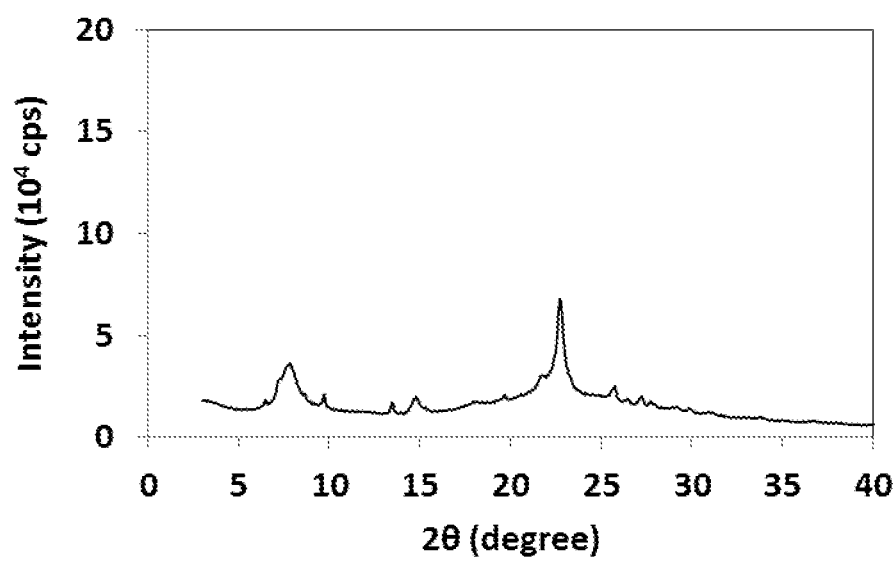

The X-ray diffraction pattern of the sample obtained is displayed in FIG. 9a, and displays the following reflections and corresponding intensities:

| Angle [2-Theta °] | Intensity [%] |
|---|---|
| 6.502 | 26.8 |
| 7.27 | 42.2 |
| 7.807 | 53.3 |
| 8.648 | 31.6 |
| 9.711 | 31.4 |
| 13.499 | 25.6 |
| 14.793 | 29.2 |
| 15.308 | 21.7 |
| 18.033 | 25.6 |
| 19.654 | 30.7 |
| 20.59 | 31 |
| 21.768 | 44.9 |
| 22.762 | 100 |
| 25.765 | 37.1 |
| 26.44 | 28.1 |
| 27.248 | 29.4 |
| 27.705 | 26.3 |
| 27.945 | 24.3 |
| 29.088 | 22.3 |
| 29.866 | 21 |
| 31.025 | 18.6 |
| 33.845 | 14.9 |
| 36.798 | 12.3 |

Figure 9B:
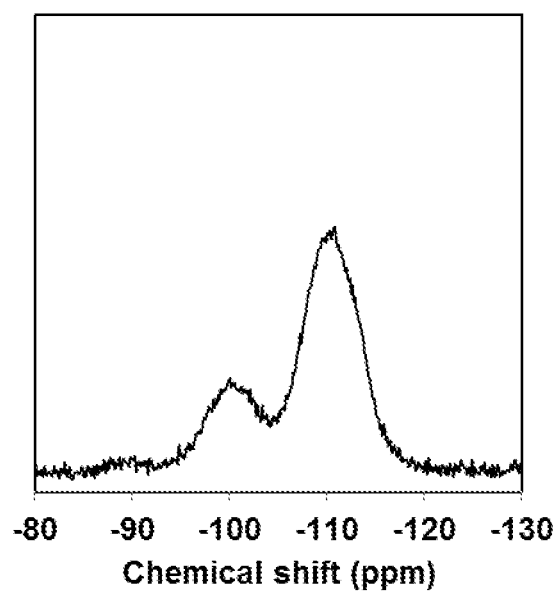

The $^{29}$Si MAS NMR of the sample obtained is displayed in FIG. 9b and revels the following signal intensities in %: −102 ppm (Q4 (1Al)+Q3) 26%, 15-108 ppm (Q4 (0Al, T3-T9)) 46%, −112 ppm (Q4 (0Al, T1-T2)) 27%.

EXAMPLE 10: Acid Treatment (6M) of Zeolite Beta (800° C./24 h) for 24 h Under Reflux The calcined sample obtained from Reference Example 2 was taken as starting material. 1 g of the white powder was dispersed in 50 ml 6 M nitric acid solution in $H_2O$ and stirred in a round bottom flask at 100° C. under reflux for 24 hours. Afterwards the solid was extracted by vacuum filtration and subsequent washing with deionized $H_2O$ until a pH of 7 was reached. Finally the obtained white powder was dried for 12 hours at 100° C. under air in a muffle furnace. Chemical analysis indicated an Si/Al molar ratio of 204 and <0.1 wt-% of $Na_2O$ on a calcined basis. The BET surface area was measured by means of nitrogen sorption at 77K afforded a value of 560 m²/g.

Figure 10A:
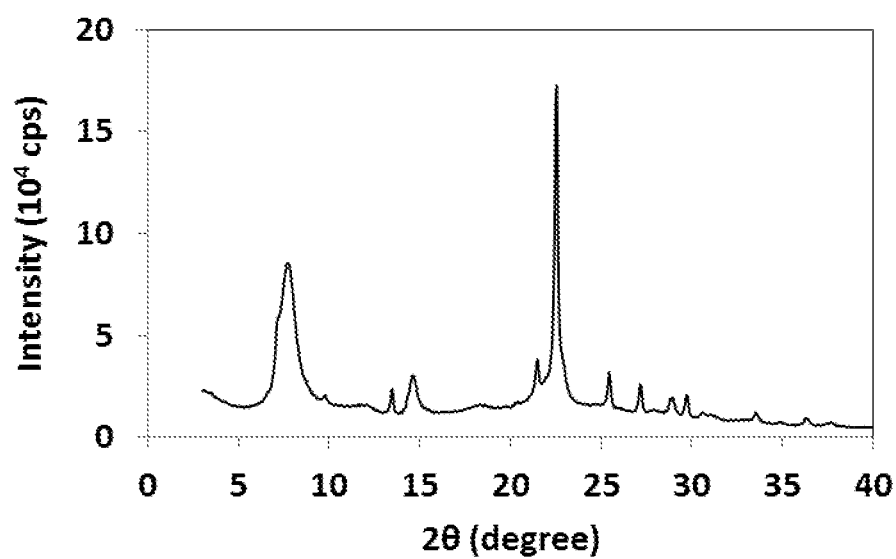

The X-ray diffraction pattern of the sample obtained is displayed in FIG. 10a, and displays the following reflections and corresponding intensities:

| Angle [2-Theta °] | Intensity [%] |
|---|---|
| 3.032 | 13.5 |
| 7.166 | 34.2 |
| 7.734 | 49.7 |
| 9.788 | 11.8 |
| 12.071 | 9.2 |
| 13.447 | 13.4 |
| 14.616 | 17.4 |
| 18.385 | 9.5 |
| 20.318 | 10.3 |
| 21.498 | 22 |
| 22.544 | 100 |
| 22.918 | 21.1 |
| 25.442 | 18.2 |
| 27.151 | 15.1 |
| 27.875 | 7.7 |
| 28.902 | 11.3 |
| 29.723 | 12.2 |
| 30.604 | 7 |
| 31.098 | 6.5 |
| 33.541 | 7.4 |
| 36.318 | 5.5 |

Figure 10B:
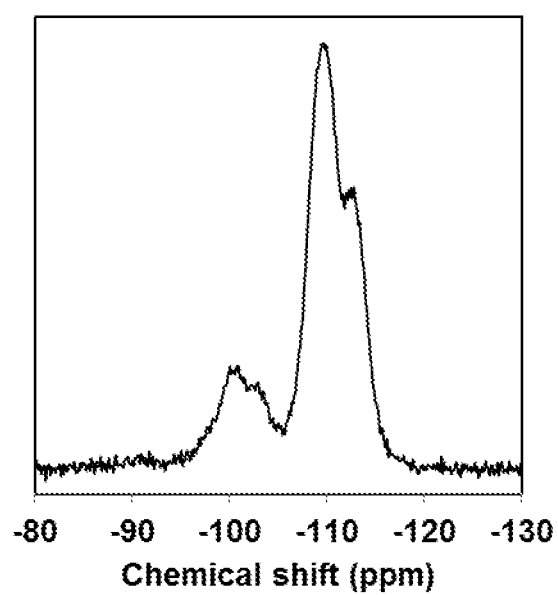

The $^{29}$Si MAS NMR of the sample obtained is displayed in FIG. 10b and revels the following signal intensities in %: −102 ppm (Q4 (1Al)+Q3) 19%, 15-108 ppm (Q4 (0Al, T3-T9)) 60%, −112 ppm (Q4 (0Al, T1-T2)) 21%.

EXAMPLE 11: Acid Treatment (6M) of Zeolite Beta (800° C./24 h) for 2 h Under Reflux The calcined sample obtained from Reference Example 2 was taken as starting material. 1 g of the white powder was dispersed in 50 ml 6 M nitric acid solution in $H_2O$ and stirred in a round bottom flask at 100° C. under reflux for 2 hours. Afterwards the solid was extracted by vacuum filtration and subsequent washing with deionized $H_2O$ until a pH of 7 was reached. Finally the obtained white powder was dried for 12 hours at 100° C. under air in a muffle furnace. Chemical analysis indicated an Si/Al molar ratio of 112 and <0.1 wt-% of $Na_2O$ on a calcined basis. The BET surface area was measured by means of nitrogen sorption at 77K afforded a value of 605 m$^2$/g.

Figure 11A:
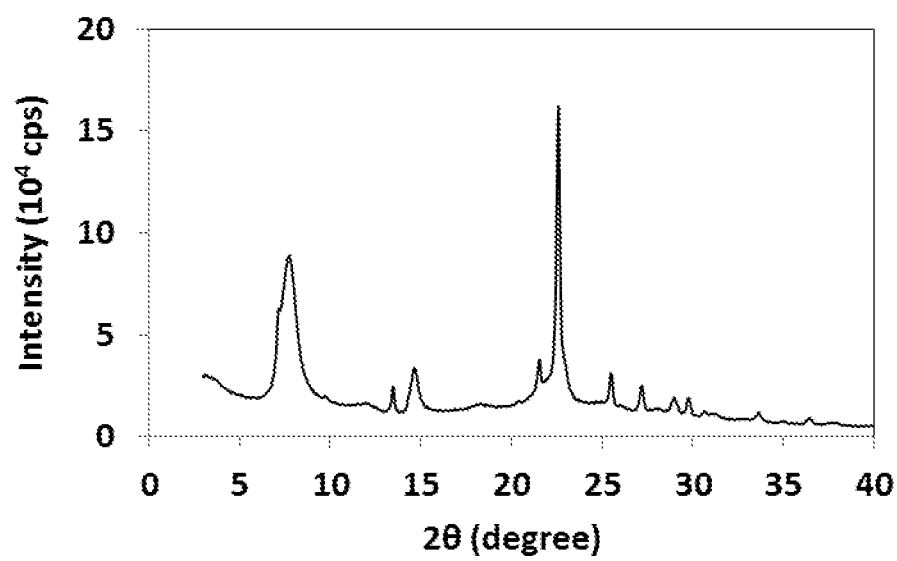

The X-ray diffraction pattern of the sample obtained is displayed in FIG. 11a, and displays the following reflections and corresponding intensities:

| Angle [2-Theta °] | Intensity [%] |
| --- | --- |
| 3.153 | 15.4 |
| 7.153 | 29.6 |
| 7.741 | 42.1 |
| 9.777 | 11.5 |
| 12.061 | 9.3 |
| 13.472 | 12.9 |
| 14.659 | 17.4 |
| 18.363 | 9.8 |
| 20.373 | 10.9 |
| 21.548 | 23.6 |
| 22.598 | 100 |
| 22.841 | 28.1 |
| 25.498 | 19.9 |
| 27.191 | 16.7 |
| 29.013 | 13 |
| 29.801 | 13 |
| 30.659 | 8.7 |
| 31.188 | 7.8 |
| 33.657 | 7.8 |
| 34.997 | 5.5 |
| 36.466 | 6.3 |

Figure 11B:
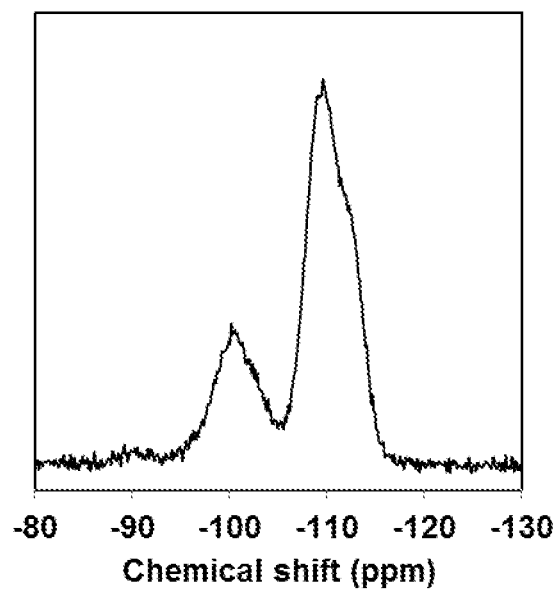
FIGS. 11c, 11d, 13c, 14c, 15c, 16c respectively display the results from methanol-to-olefin (MTO) catalytic testing obtained using the samples from Reference Examples 11, 13, and 14, and Comparative Examples 15 and 16. In the figures, the "time on stream" in hours is plotted along the abscissa, and the conversion rate "●" in % as well as the selectivities in % relative to specific compounds in the product stream including propene "■" and butene "◆" are plotted along the ordinate.
Figure 11C:
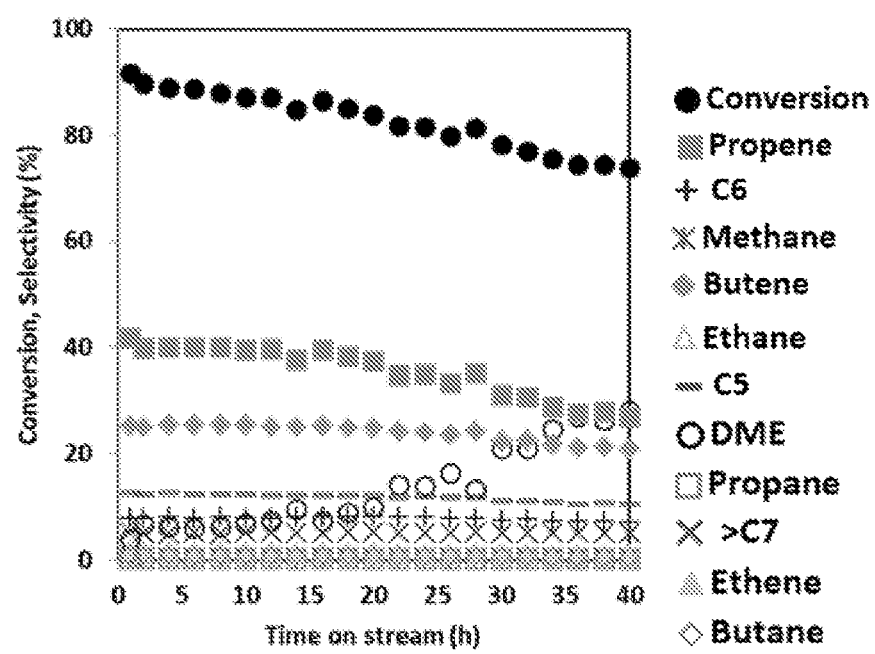

The $^{29}$Si MAS NMR of the sample obtained is displayed in FIG. 11b and revels the following signal intensities in %: −102 ppm (Q4 (1Al)+Q3) 24%, 15-108 ppm (Q4 (0Al, T3-T9)) 54%, −112 ppm (Q4 (0Al, T1-T2)) 21%.

Figure 11D:
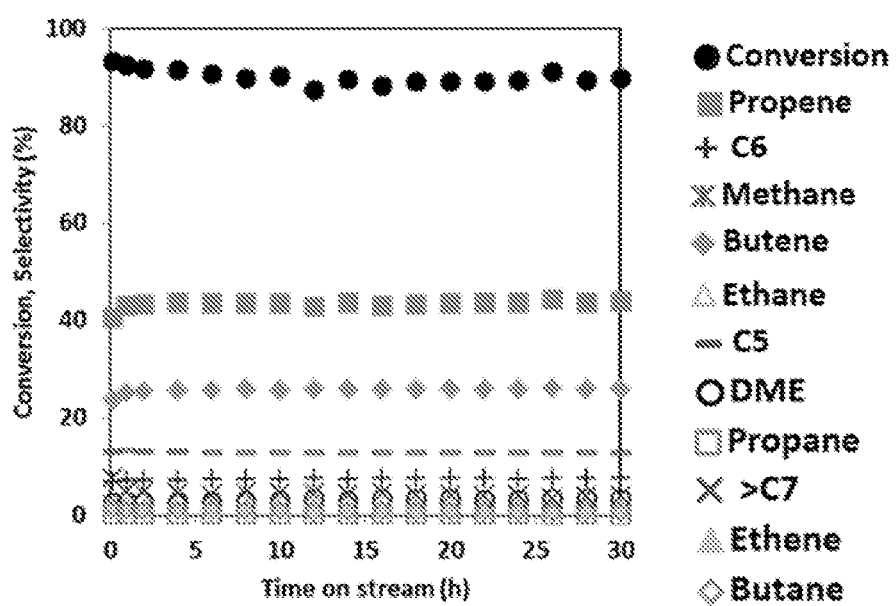

The catalyst sample was tested in the conversion of methanol to olefins. The testing conditions were as follows: $P_{MeOH}$=50 kPa, Catalyst, 0.05 g; Catalyst bed height 1-1.5 cm, MeOH liquid, 6.75 μl/min; He gas, 4.1 ml/min; Temperature, 500° C. The product stream was analyzed with a GC-FID detector from Shimazu GC-2014 applying a Divinylbenzene-styrene Copolymer column (J&W, HP-PLOT Q). The test was run at a load of W/F=5 g·h/mol, the results of which are displayed in FIG. 11 c, as well as at a load of W/F=10 g·h/mol, the results of which are displayed in FIG. 11d.

Thus, as may be taken from the results from testing in the conversion of methanol to olefins obtained for the present inventive example, not only may a conversion rate be achieved at high selectivities for the conversion of methanol to propene and butene, respectively, but said high conversion and selectivities may quite unexpectedly be maintained for a long period of time on stream without the slightest decrease. In particular, as compared to the results achieved for the comparative examples (cf. FIGS. 15c and 16c for Comparative Examples 15 and 16, respectively), far higher yields of propene and butene may be obtained at far higher overall selectivities due to the extremely constant conversion rate and selectivies leading to unprecedented times on stream prior to the regeneration of the catalyst. Accordingly, as demonstrated by the present results from comparative testing, a highly efficient catalyst is provided by the present invention compared to the commercial catalysts exemplified by Comparative Examples 15 and 16 below.

EXAMPLE 12: Acid Treatment (3M) of Zeolite Beta (800° C./24 h) for 2 h Under Reflux The calcined sample obtained from Reference Example 2 was taken as starting material. 1 g of the white powder was dispersed in 50 ml 3 M nitric acid solution in $H_2O$ and stirred in a round bottom flask at 100° C. under reflux for 2 hours. Afterwards the solid was extracted by vacuum filtration and subsequent washing with deionized $H_2O$ until a pH of 7 was reached. Finally the obtained white powder was dried for 12 hours at 100° C. under air in a muffle furnace. Chemical analysis indicated a Si/Al ratio of 92 and <0.1 wt-% of $Na_2O$ on a calcined basis. The BET surface area was measured by means of nitrogen sorption at 77K afforded a value of 621 m$^2$/g.

Figure 12A:
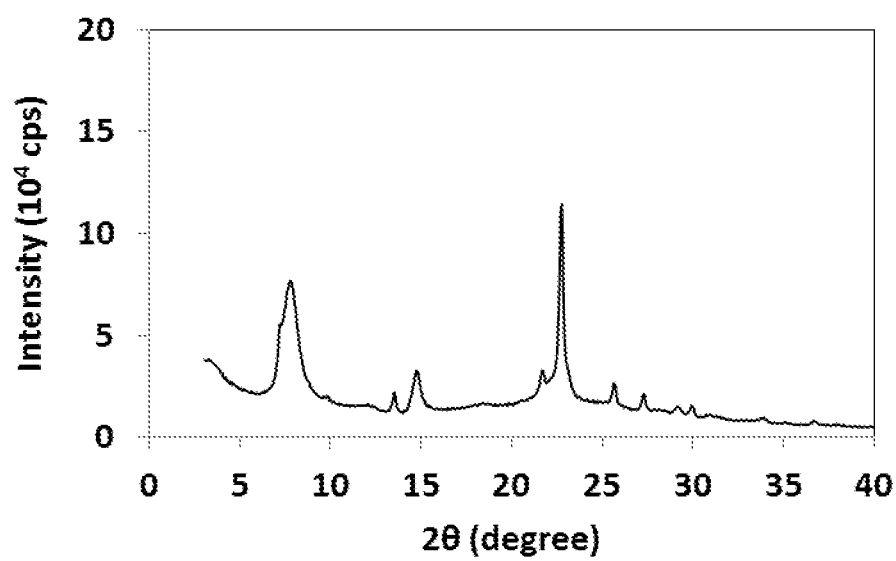

The X-ray diffraction pattern of the sample obtained is displayed in FIG. 12a, and displays the following reflections and corresponding intensities:

| Angle [2-Theta °] | Intensity [%] |
| --- | --- |
| 3.242 | 33.8 |
| 7.205 | 48.3 |
| 7.781 | 66.6 |
| 9.821 | 17.7 |
| 12.102 | 14 |
| 13.527 | 19.2 |
| 14.75 | 28.4 |
| 18.353 | 14.7 |
| 20.511 | 15.9 |
| 21.667 | 28.8 |
| 22.755 | 100 |
| 23.086 | 28.9 |
| 25.651 | 23.2 |
| 27.292 | 18.4 |
| 28.192 | 11.9 |
| 29.159 | 13.6 |
| 29.944 | 13.6 |
| 30.943 | 9.5 |
| 31.443 | 8.9 |
| 33.857 | 8.5 |
| 36.687 | 6.9 |

Figure 12B:
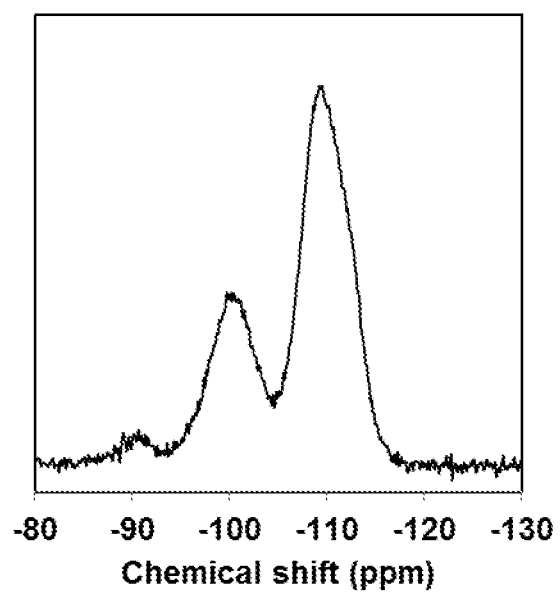

The $^{29}$Si MAS NMR of the sample obtained is displayed in FIG. 12b and revels the following signal intensities in %: −102 ppm (Q4 (1Al)+Q3) 30%, 15-108 ppm (Q4 (0Al, T3-T9)) 49%, −112 ppm (Q4 (0Al, T1-T2)) 18%.

EXAMPLE 13: Acid Treatment (1 M) of Zeolite Beta (800° C./24 h) for 2 h Under Reflux The calcined sample obtained from Reference Example 2 was taken as starting material. 1 g of the white powder was dispersed in 50 ml 1 M nitric acid solution in $H_2O$ and stirred in a round bottom flask at 100° C. under reflux for 2 hours. Afterwards the solid was extracted by vacuum filtration and subsequent washing with deionized H₂O until a pH of 7 was reached. Finally the obtained white powder was dried for 12 hours at 100° C. under air in a muffle furnace. Chemical analysis indicated a Si/Al ratio of 80 and <0.1 wt-% of Na₂O on a calcined basis. The BET surface area was measured by means of nitrogen sorption at 77K affording a value of 569 m²/g.

Figure 13A:
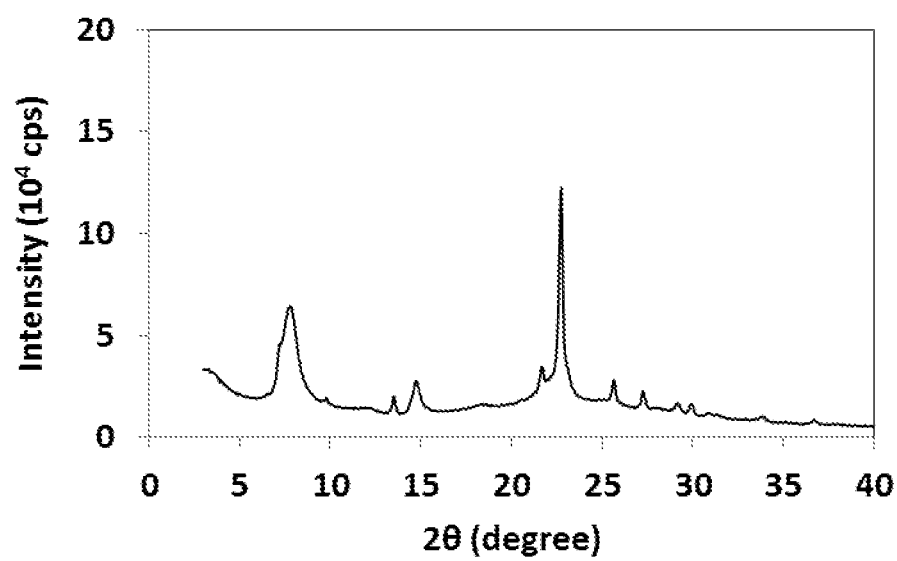

The X-ray diffraction pattern of the sample obtained is displayed in FIG. 13a, and displays the following reflections and corresponding intensities:

| Angle [2-Theta °] | Intensity [%] |
|---|---|
| 3.214 | 27.3 |
| 6.538 | 17.8 |
| 7.197 | 37.6 |
| 7.802 | 52.9 |
| 9.812 | 15.9 |
| 12.121 | 12 |
| 13.497 | 16.5 |
| 14.729 | 22.6 |
| 18.31 | 13.5 |
| 20.512 | 15.3 |
| 21.708 | 28.5 |
| 22.745 | 100 |
| 23.104 | 27.7 |
| 25.649 | 22.6 |
| 27.254 | 18.3 |
| 27.972 | 12 |
| 29.156 | 13.9 |
| 29.949 | 13.7 |
| 30.862 | 9.7 |
| 31.35 | 8.9 |
| 33.855 | 8.5 |
| 36.695 | 6.9 |

Figure 13B:
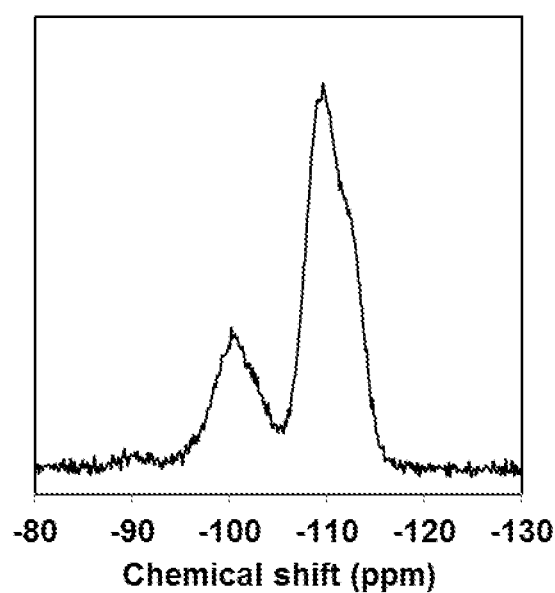

The $^{29}$Si MAS NMR of the sample obtained is displayed in FIG. 13b and revels the following signal intensities in %: −102 ppm (Q4 (1Al)+Q3) 27%, 15-108 ppm (Q4 (0Al, T3-T9)) 53%, −112 ppm (Q4 (0Al, T1-T2)) 19%.

Figure 13C:
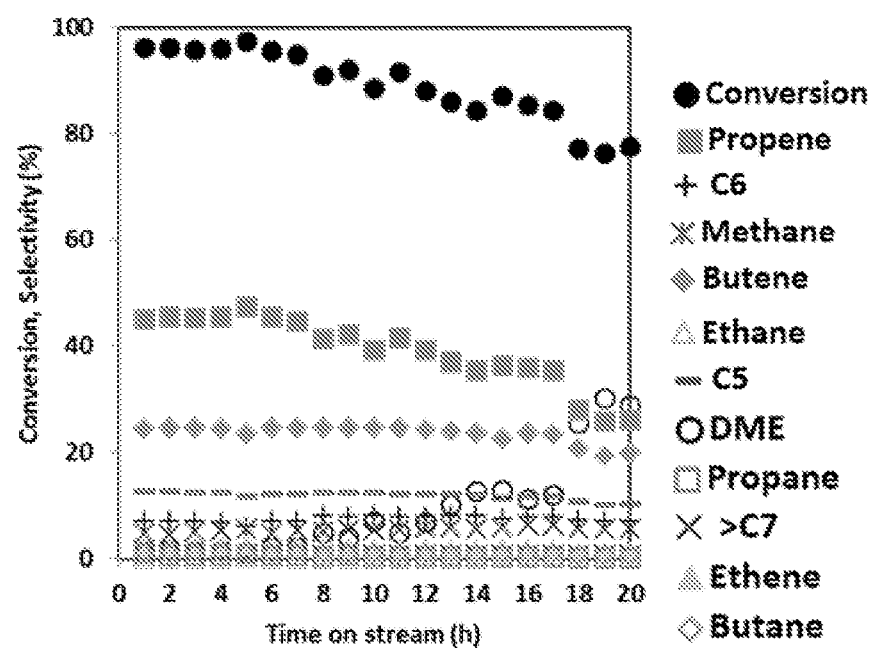

The catalyst sample was tested in the conversion of methanol to olefins. The testing conditions were as follows: W/F=5 g·h/mol, $P_{MeOH}$=50 kPa, Catalyst, 0.05 g; Catalyst bed height 1-1.5 cm, MeOH liquid, 6.75 μl/min; He gas, 4.1 ml/min; $P_{MeOH}$=50 kPa; Temperature, 500° C. The product stream was analyzed with a GC-FID detector from Shimazu GC-2014 applying a Divinylbenzene-styrene Copolymer column (J&W, HP-PLOT Q), the results of which are displayed in FIG. 13c.

EXAMPLE 14: Acid Treatment (1 M) of Zeolite Beta (800° C./24 h) for 24 h at Ambient Temperature The calcined sample obtained from Reference Example 2 was taken as starting material. 1 g of the white powder was dispersed in 50 ml 1 M nitric acid solution in H₂O and stirred in a round bottom flask at 25° C. for 24 hours. Afterwards the solid was extracted by vacuum filtration and subsequent washing with deionized H₂O until a pH of 7 was reached. Finally the obtained white powder was dried for 12 hours at 100° C. under air in a muffle furnace. Chemical analysis indicated a Si/Al ratio of 50 and <0.1 wt-% of Na₂O on a calcined basis. The BET surface area was measured by means of nitrogen sorption at 77K affording a value of 572 m²/g.

Figure 14A:
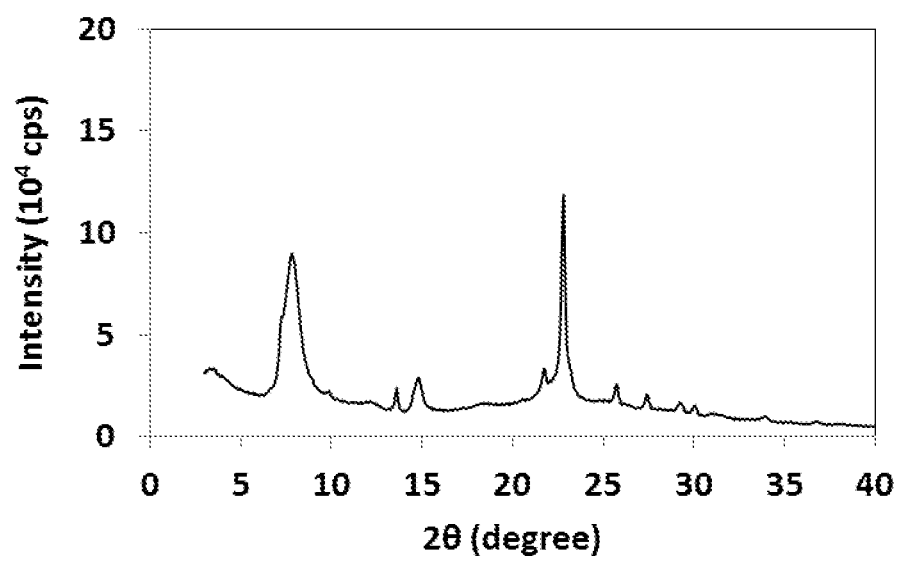

The X-ray diffraction pattern of the sample obtained is displayed in FIG. 14a, and displays the following reflections and corresponding intensities:

| Angle [2-Theta °] | Intensity [%] |
|---|---|
| 3.361 | 28.2 |
| 7.252 | 49.6 |
| 7.812 | 76.2 |
| 9.817 | 18.6 |
| 12.113 | 14.6 |
| 13.592 | 20.2 |
| 14.789 | 24.6 |
| 18.31 | 14.1 |
| 20.634 | 15.7 |
| 21.747 | 28.3 |
| 22.806 | 100 |
| 23.156 | 29.5 |
| 25.747 | 21.6 |
| 27.405 | 17.6 |
| 29.244 | 14.1 |
| 30.034 | 13 |
| 31.018 | 9.8 |
| 31.484 | 9.1 |
| 33.932 | 8.6 |
| 36.781 | 6.5 |

Figure 14B:
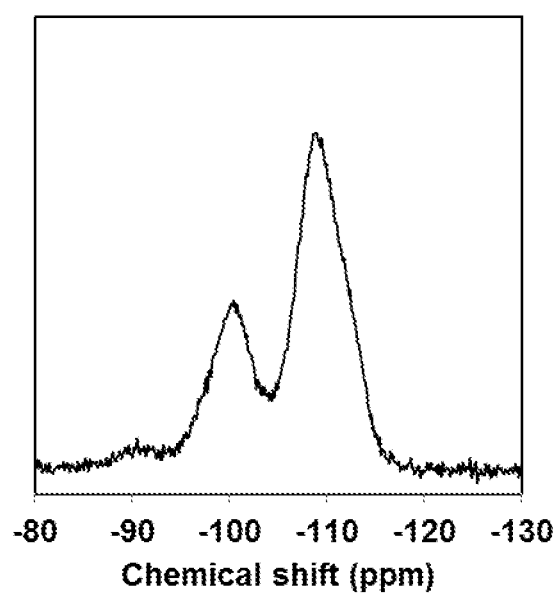

The $^{29}$Si MAS NMR of the sample obtained is displayed in FIG. 14b and revels the following signal intensities in %: −102 ppm (Q4 (1Al)+Q3) 30%, 15-108 ppm (Q4 (0Al, T3-T9)) 51%, −112 ppm (Q4 (0Al, T1-T2)) 18%.

Figure 14C:
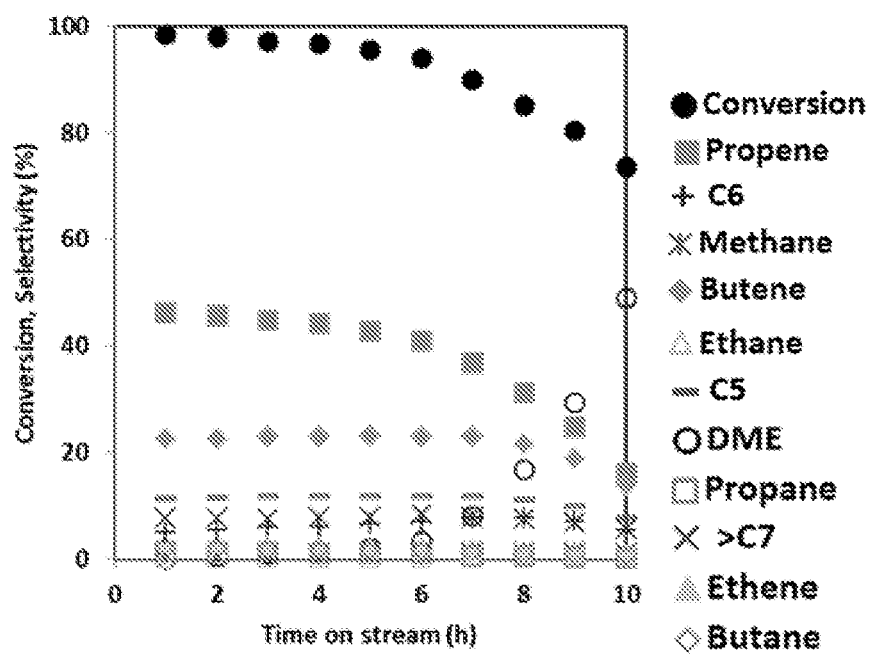

The catalyst sample was tested in the conversion of methanol to olefins. The testing conditions were as follows: W/F=5 g·h/mol, $P_{MeOH}$=50 kPa, Catalyst, 0.05 g; Catalyst bed height 1-1.5 cm, MeOH liquid, 6.75 μl/min; He gas, 4.1 ml/min; $P_{MeOH}$=50 kPa; Temperature, 500° C. The product stream was analyzed with a GC-FID detector from Shimazu GC-2014 applying a Divinylbenzene-styrene Copolymer column (J&W, HP-PLOT Q), the results of which are displayed in FIG. 14c.

COMPARATIVE EXAMPLE 15: Zeolite Beta from Templated Synthesis (Si/Al=150)

As a comparative Example, a commercial sample of zeolite beta as obtained from template synthesis (product name: CP811C-300; Zeolyst International) was employed. Chemical analysis indicated an Si/Al molar ratio of 150 and <0.1 wt-% of Na₂O on a calcined basis. The BET surface area was measured by means of nitrogen sorption at 77K afforded a value of 585 m²/g.

Figure 15A:
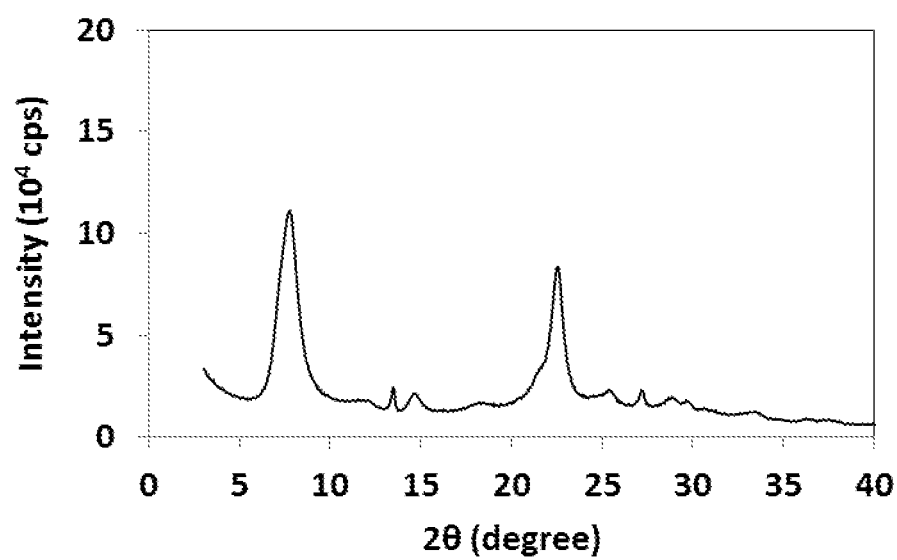

The X-ray diffraction pattern of the sample obtained is displayed in FIG. 15a, and displays the following reflections and corresponding intensities:

| Angle [2-Theta °] | Intensity [%] |
|---|---|
| 7.732 | 100 |
| 11.441 | 16.5 |
| 12.003 | 16.2 |
| 13.511 | 22.1 |
| 14.664 | 19.3 |
| 18.241 | 15.4 |
| 21.552 | 30.1 |
| 22.557 | 75 |
| 24.952 | 19 |
| 25.454 | 20.5 |
| 27.199 | 20.6 |
| 28.825 | 17.3 |
| 29.653 | 15.7 |
| 30.687 | 12.9 |
| 33.407 | 11.2 |
| 36.334 | 8.1 |
| 37.546 | 8.1 |

Figure 15B:
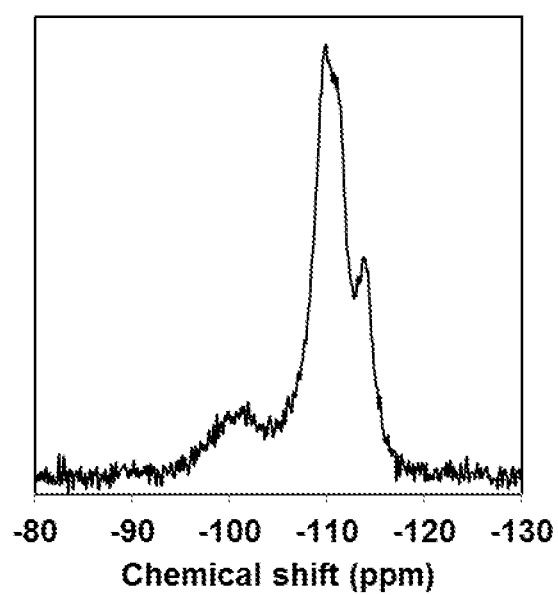
Figure 15C:
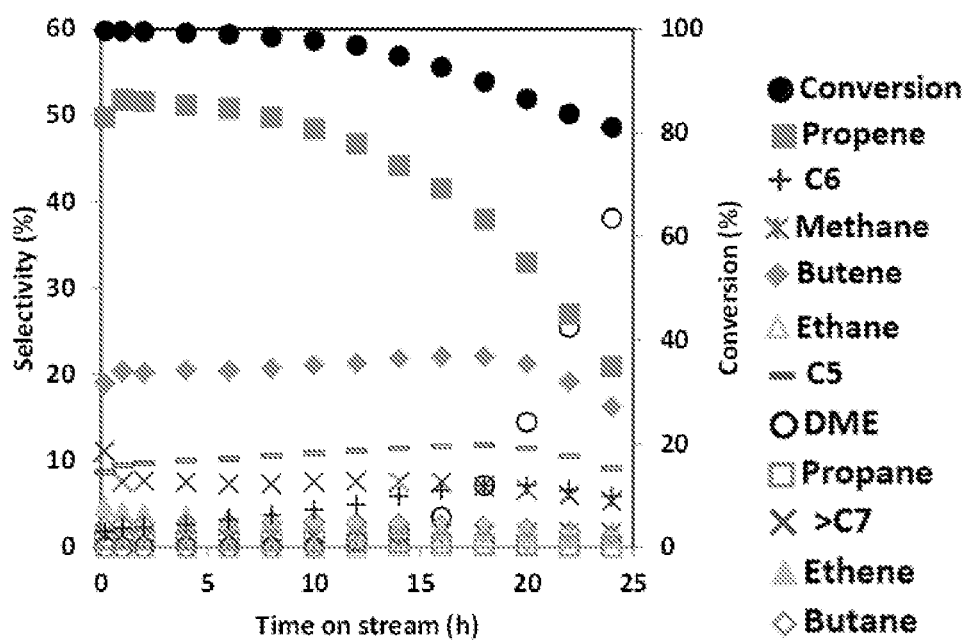

The $^{29}$Si MAS NMR of the sample obtained is displayed in FIG. 15b and revels the following signal intensities in %: −102 ppm (Q4 (1Al)+Q3) 18%, 15-108 ppm (Q4 (0Al, T3-T9)) 62%, −112 ppm (Q4 (0Al, T1-T2)) 19%.

The catalyst sample was tested in the conversion of methanol to olefins. The testing conditions were as follows: W/F=10 g·h/mol, $P_{MeOH}$=50 kPa, Catalyst, 0.05 g; Catalyst bed height 1-1.5 cm, MeOH liquid, 6.75 μl/min; He gas, 4.1 ml/min; Temperature, 500° C. The product stream was analyzed with a GC-FID detector from Shimazu GC-2014 applying a Divinylbenzene-styrene Copolymer column (J&W, HP-PLOT Q), the results of which are displayed in FIG. 15c.

Thus, as may be taken from the results from testing in the conversion of methanol to olefins, compared to the results obtained for inventive Example 11 under the same testing conditions (cf. catalytic testing results in FIG. 11d), both the conversion rate and the propene selectivity already begin to decline after a few hours on stream and increasing drop when the reaction is further conducted whereas quite surprisingly both the conversion rate and the propene selectivity achieved for the inventive example remains practically constant even after 30 hours on stream. Same applies with respect to the selectivity of the reaction towards butene which, again, remains constant for the inventive example even after 30 hours on stream, whereas in the present comparative example the selectivity begins to rapidly drop after 20 hours on stream.

COMPARATIVE EXAMPLE 16: Zeolite Beta from Templated Synthesis (Si/Al=250)

As a comparative Example, a commercial sample of zeolite beta as obtained from template synthesis (product name: HSZ-980HOA; Tosoh Corp.) was employed. Chemical analysis indicated a Si/Al ratio of 250 and <0.1 wt-% of Na$_2$O on a calcined basis. The BET surface area was measured by means of nitrogen sorption at 77K of 590 m$^2$/g.

Figure 16A:
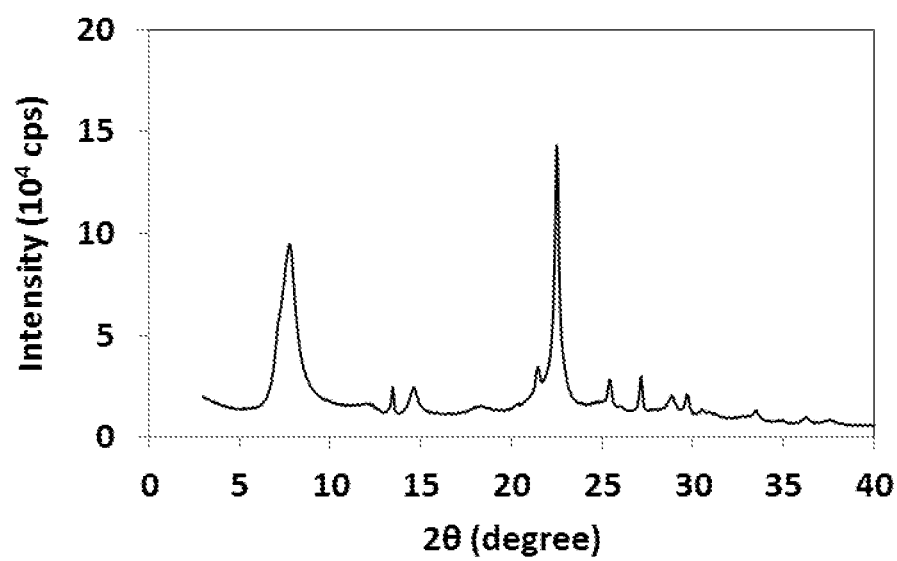

The X-ray diffraction pattern of the sample obtained is displayed in FIG. 16a, and displays the following reflections and corresponding intensities:

| Angle [2-Theta °] | Intensity [%] |
|---|---|
| 7.133 | 40.7 |
| 7.768 | 66.2 |
| 12.084 | 11.8 |
| 13.463 | 16.8 |
| 14.613 | 17 |
| 18.284 | 10.9 |
| 20.408 | 11.7 |
| 21.464 | 24.1 |
| 22.52 | 100 |
| 24.605 | 12.2 |
| 25.415 | 19.5 |
| 26.053 | 10.7 |
| 27.152 | 20.9 |
| 28.833 | 14.2 |
| 29.697 | 14.6 |
| 30.543 | 9.3 |
| 30.933 | 8.6 |
| 32.691 | 7.3 |
| 33.518 | 9.3 |
| 34.862 | 6.1 |
| 36.253 | 7 |
| 37.494 | 5.9 |

Figure 16B:
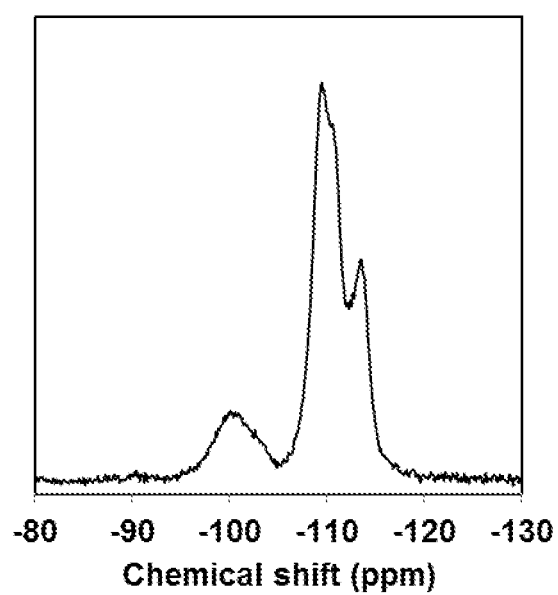
Figure 16C:
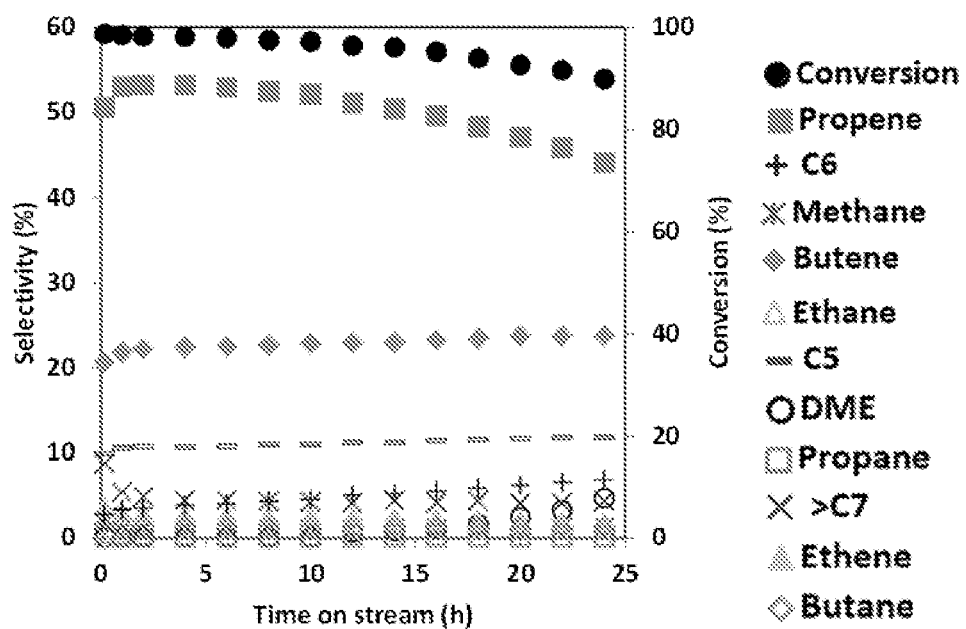

The $^{29}$Si MAS NMR of the sample obtained is displayed in FIG. 16b and revels the following signal intensities in %: −102 ppm (Q4 (1Al)+Q3) 16%, 15-108 ppm (Q4 (0Al, T3-T9)) 63%, −112 ppm (Q4 (0Al, T1-T2)) 21%.

The catalyst sample was tested in the conversion of methanol to olefins. The testing conditions were as follows: W/F=10 g·h/mol, $P_{MeOH}$=50 kPa, Catalyst, 0.05 g; Catalyst bed height 1-1.5 cm, MeOH liquid, 6.75 μl/min; He gas, 4.1 ml/min; Temperature, 500° C. The product stream was analyzed with a GC-FID detector from Shimazu GC-2014 applying a Divinylbenzene-styrene Copolymer column (J&W, HP-PLOT Q), the results of which are displayed in FIG. 16c.

As for Comparative Example 15, as may be taken from the results from testing in the conversion of methanol to olefins, compared to the results obtained for inventive Example 11 under the same testing conditions (cf. catalytic testing results in FIG. 11d), both the conversion rate and the propene selectivity already begin to decline after a few hours on stream and constantly drop when the reaction is further conducted whereas quite surprisingly both the conversion rate and the propene selectivity achieved for the inventive example remains practically constant even after 30 hours on stream. In particular, although both the conversion rate and the propene selectivity are initially higher in the present comparative example, this is quickly compensated by the constant conversion rate and propene selectivity observed for inventive Example 11, such that unexpectedly higher yields may be obtained when employing the inventive catalaysts, not only due to the greater overal conversion and selectivity, but in particular in view of the far longer time on stream which is possible prior to the regeneration of the catalyst. As a result, an extremely efficient catalyst for the conversion of methanol to olefins is provided by the present invention.

The invention claimed is:

1. A method for the preparation of a treated zeolitic material having a BEA framework structure comprising the steps of:
   (i) using an organotemplate-free synthetic process to provide a zeolitic material having a BEA framework structure, wherein the BEA framework structure comprises YO$_2$ and X$_2$O$_3$, wherein Y is a tetravalent element, and X is a trivalent element, wherein the zeolitic material provided in step (i) is non-calcined;
   (ii) calcining the zeolitic material provided in step (i) at a temperature of 650° C. or more; and
   (iii) treating the calcined zeolitic material obtained from step (ii) with an aqueous solution having a pH of 5 or less,
   wherein step (iii) is performed at ambient temperature.

2. The method of claim 1, wherein in step (ii) the zeolitic material provided in step (i) is calcined at a temperature comprised in the range of from 680° C. to 1000° C.

3. The method of claim 1, wherein calcining in step (ii) is conducted in an atmosphere containing 10 wt.-% or less of water.

4. The method of claim 1, wherein Y is selected from the group consisting of Si, Sn, Ti, Zr, Ta, Fe, Ge, and combinations of two or more thereof.

5. The method of claim 1, wherein X is selected from the group consisting of Al, B, In, Ga, and combinations of two or more thereof.

6. A zeolitic material having a BEA framework structure obtained according to a method as defined in claim 1.

7. The zeolitic material of claim 6 having a BEA framework structure having an X-ray diffraction pattern comprising at least the following reflections:

| Intensity (%) | Diffraction angle 2θ/° [Cu K(alpha 1)] |
|---|---|
| [8-46] | [21.49-21.79] |
| 100 | [22.55-22.85] |
| [7-37] | [25.45-25.75] |
| [5-30] | [27.10-27.40] |
| [4-23] | [28.96-29.26] |
| [4-23] | [29.75-30.05] |
| [2-14] | [33.64-33.94] | wherein 100% relates to the intensity of the maximum peak in the X-ray diffraction pattern, and wherein the BEA framework structure comprises $YO_2$ and $X_2O_3$, wherein Y is a tetravalent element, and X is a trivalent element.

8. The zeolitic material of claim 6, wherein the $^{29}$Si MAS NMR spectrum of the zeolitic material comprises:

one or more peaks (P'1) in the range of from −95 to −104.5 ppm; and one or more peaks (P'2) in the range of from −105 to −116 ppm;

wherein the ratio of the total integration value of the one or more peaks (P'1) to the one or more peaks (P'2) is comprised in the range of from 19:81 to 35:65.

9. The zeolitic material of claim 6 having a BEA framework structure, wherein the BEA framework structure comprises $YO_2$ and $X_2O_3$, wherein Y is a tetravalent element, and X is a trivalent element, and wherein the $^{27}$Al MAS NMR of the zeolitic material comprises:

a first peak (P1) in the range of from 45 to 65 ppm;

a second peak (P2) in the range of from 11 to 44 ppm; and a third peak (P3) in the range of from −10 to 10 ppm;

wherein the integration of the first, second, and third peaks in the $^{27}$Al MAS NMR of the zeolitic material offers ratios of the integration values P1:P2:P3 comprised in the range of from 1:(0.1−0.8):(0.4−0.9).

10. The zeolitic material of claim 6, wherein Y is selected from the group consisting of Si, Sn, Ti, Zr, Ta, Fe, Ge, and combinations of two or more thereof.

11. The zeolitic material of claim 6, wherein X is selected from the group consisting of Al, B, In, Ga, and combinations of two or more thereof.

12. A process for converting oxygenates to olefins, comprising:

(1) providing a gas stream comprising one or more oxygenates;

(2) contacting the gas stream with a catalyst comprising a zeolitic material according to claim 6.

* * * * *